US007960173B2

(12) United States Patent
White et al.

(10) Patent No.: US 7,960,173 B2
(45) Date of Patent: Jun. 14, 2011

(54) CARDIAC CONDUCTION SYSTEM CELLS AND USES THEREOF

(75) Inventors: Steven M. White, New Orleans, LA (US); William C. Claycomb, Carriere, MS (US)

(73) Assignee: Board of Supervisors of Louisiana State University and Agricultural and Mechanical College, Baton Rouge, LA (US)

(*) Notice: Subject to any disclaimer, the term of this patent is extended or adjusted under 35 U.S.C. 154(b) by 0 days.

(21) Appl. No.: 11/753,719

(22) Filed: May 25, 2007

(65) Prior Publication Data

US 2007/0239136 A1 Oct. 11, 2007

Related U.S. Application Data

(62) Division of application No. 10/960,644, filed on Oct. 7, 2004, now abandoned.

(60) Provisional application No. 60/578,676, filed on Jun. 10, 2004.

(51) Int. Cl.
*C12N 5/00* (2006.01)
*C12N 15/11* (2006.01)

(52) U.S. Cl. .................................. 435/325; 536/23.1

(58) Field of Classification Search .................. 435/325; 536/23.1
See application file for complete search history.

(56) References Cited

U.S. PATENT DOCUMENTS

| | | | |
|---|---|---|---|
| 5,166,065 A | 11/1992 | Williams et al. |
| 5,187,077 A | 2/1993 | Gearing et al. |
| 5,602,301 A | 2/1997 | Field |
| 5,639,618 A | 6/1997 | Gay |
| 5,733,727 A | 3/1998 | Field |
| 5,990,092 A | 11/1999 | Walsh |
| 6,146,888 A | 11/2000 | Smith et al. |
| 6,184,035 B1 | 2/2001 | Ceste et al. |
| 6,387,369 B1 | 5/2002 | Pittenger et al. |
| RE37,978 E | 2/2003 | Field |
| 6,534,052 B1 | 3/2003 | Xiao et al. |
| 6,576,464 B2 | 6/2003 | Gold et al. |
| 6,589,728 B2 | 7/2003 | Csete et al. |
| 6,602,711 B1 | 8/2003 | Thomson et al. |
| 6,607,720 B1 | 8/2003 | Xiao et al. |
| 6,642,048 B2 | 11/2003 | Xu et al. |
| 6,673,604 B1 | 1/2004 | Edge |
| 6,737,054 B2 | 5/2004 | Field |
| 2001/0016193 A1 | 8/2001 | Engler et al. |
| 2002/0001577 A1 | 1/2002 | Haverich et al. |
| 2002/0022259 A1 | 2/2002 | Lee et al. |
| 2002/0045259 A1 | 4/2002 | Lim et al. |
| 2002/0061587 A1 | 5/2002 | Anversa |
| 2002/0127715 A1 | 9/2002 | Benvenisty et al. |
| 2002/0142457 A1 | 10/2002 | Umezawa et al. |
| 2003/0017589 A1 | 1/2003 | Mandalam et al. |
| 2003/0022367 A1 | 1/2003 | Xu |
| 2003/0040111 A1 | 2/2003 | Gold et al. |
| 2003/0082152 A1 | 5/2003 | Hedrick et al. |
| 2003/0104568 A1 | 6/2003 | Lee |
| 2003/0119107 A1 | 6/2003 | Dang et al. |
| 2003/0157494 A1 | 8/2003 | Van Eijs et al. |
| 2003/0211088 A1 | 11/2003 | Field |
| 2003/0224345 A1 | 12/2003 | West et al. |
| 2004/0005295 A1 | 1/2004 | Lee |
| 2004/0033601 A1 | 2/2004 | Davidson |
| 2004/0096967 A1 | 5/2004 | Gryseels et al. |
| 2004/0106095 A1 | 6/2004 | Thomson et al. |
| 2004/0126879 A1 | 7/2004 | Schneider et al. |
| 2004/0254134 A1 | 12/2004 | Marban et al. |
| 2005/0031600 A1 | 2/2005 | Mickle et al. |
| 2005/0037488 A1 | 2/2005 | Mitalipova et al. |
| 2005/0037489 A1 | 2/2005 | Gestein et al. |
| 2005/0054092 A1 | 3/2005 | Xu et al. |
| 2005/0059145 A1 | 3/2005 | Schoonjans |
| 2005/0181502 A1 | 8/2005 | Reyes |
| 2005/0227353 A1 | 10/2005 | Mummery |
| 2005/0250202 A1 | 11/2005 | March et al. |

FOREIGN PATENT DOCUMENTS

WO WO98/189906 * 7/1998
WO WO/00/17326 3/2000

OTHER PUBLICATIONS

Fujikura et al (Genes & Development, 16: 784-789, 2002.*
Lien et al (Development 126: 75-84, 1999).*
Gepstein et al (Expert Opin Biol Ther, 5(12): 1531-1537, 2005).*
Rosen et al (Cardiovasc Res (2004) 64 (1): 12-23. 2004).*
Anderson, R.H. et al., "The Architecture of the Sinus Node, the Atrioventricular Conduction Axis, and . . . ," J Cardiovasc Electrophysiol, vol. 9, pp. 1233-1248 (1998).
Banach, K. et al., "Development of Electrical Activity in Cardiac Myocyte Aggregates Derived from Mouse Embryonic Stem Cells," Am J Physiol Heart Circ Physiol, vol. 284, p. H2114 (2003).
Bettahi, I, et. al., "Contribution of the Kir3.1 Subunit to the Muscarinic-gated Atrial Potassium Channel IKACh," J Biol Chem, vol. 277, pp. 48282-48288 (2002).
Boyett, M.R. et al., "Sophisticated Architecture is Required for the Sinoatrial Node to Perform its Normal Pacemaker Function," J Cardiovasc Electrophysiol, vol. 14, pp. 104-106 (2003).
Boyett, M.R.et al, "The Sinoatrial Node, A Heterogeneous Pacemaker Structure," Cardiovasc Res, vol. 47, pp. 658-687 (2000).
Brewer, A. et al., "The Human and Mouse GATA-6 Genes Utilize Two Promoters and Two Initiation Codons," J Biol Chem, vol. 274, p. 38004 (1999).

(Continued)

Primary Examiner — Thaian N Ton
Assistant Examiner — Magdalene Sgagias
(74) Attorney, Agent, or Firm — Bonnie J. Davis; John H. Runnels

(57) ABSTRACT

Isolation and amplification of cardiac pacemaking/conduction system cells and development of a pacemaking/conduction system in vitro using the expression of surrogate expression markers. Use of markers to identify and select for clusters of pacemaking "nodes" that are functionally coupled with adjacent contracting regions and generation of cell populations displaying electrical properties characteristic of specialized pacemaking/conducting cardiac myocytes for modeling the cardiac conduction system, testing of pharmaceuticals and for transplantation.

1 Claim, 7 Drawing Sheets

OTHER PUBLICATIONS

Figure 1:
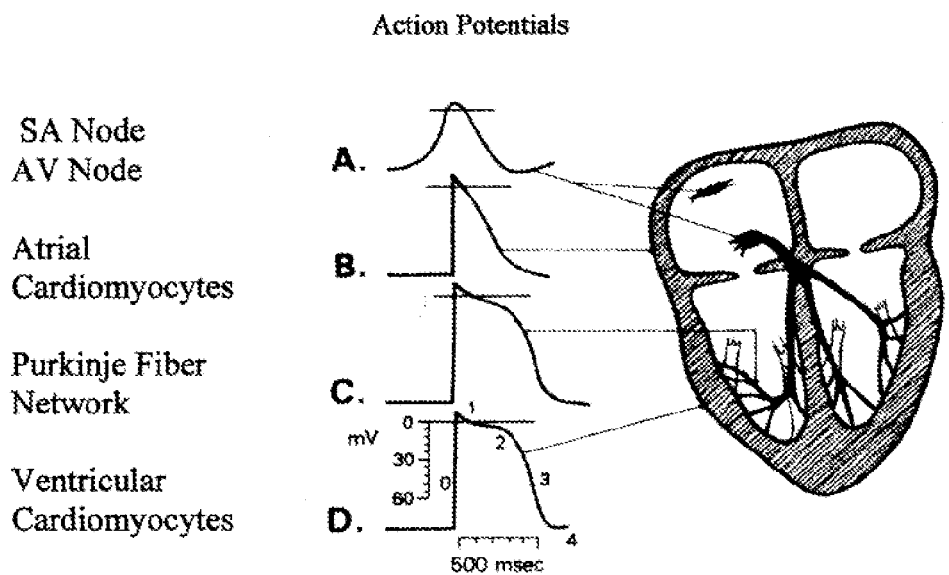

Brewer, A. et al., "Widespread Expression of an Extended Peptide Sequence of GATA-6 . . . ," Gene Expression Patterns, vol. 2, pp. 123-131 (2002).

Brutsaert, D.L. et al., "Cardiac Endothelial-Myocardial Signaling: its Role in Cardiac Growth, Contractile, Performance, and Rhythmicity," Physiol Rev, vol. 83, pp. 58-115 (2003).

Brutsaert, D.L. et al., "Cardiac Endothelium and Myocardial Functional," Cardiovasc Res, vol. 38, pp. 281-290 (1998).

Buehr, M. et al., "Rapid Loss of Oct-4 and Pluripotency in Cultured Rodent Blastocysts and Derivative Cell Lines," Viol Reprod, vol. 68, pp. 222-229 (2003).

Carlson, M.R. et al., "Expression of Msx-2 During Development, Regeneration, and Wound Healing in Axolotl Limbs," J Exp Zool, vol. 282, pp. 715-723 (1998).

Chan-Thomas, P.S. et al., "Expression of Homeobox Genes Msx-1 (Hox-7) and Msx-2 (Hox-8) during Cardiac Development in the Chick," Dev Dyn, vol. 197, pp. 203-216 (1993).

Cheng, C.F. et al., "Genetic Modificers of Cardiac Arrhythmias," Trends Mol Med, vol. 9, p. 59 (2003).

Chien, K.R. et al., "Regulation of Cardiac Gene Expression During Myocardial Growth and Hypertrophy: Molecular Studies of An adaptive Physiologic Response," FASEB J, vol. 5, p. 3037 (1991).

Cho, H.S. et al., "The Electrophysiological Properties of Spontaneously Beating Pacemaker Cells Isolated From Mouse Sinoatrial Node," J Physiol, vol. 550, pp. 169-180 (2003).

Christoffels, V.M. et al., "Chamber Formation and Morphogenesis in the Developing Mammalian Heart," Dev Biol, vol. 223, pp. 266-278 (2000).

Claycomb, W.C. et al., "HL-1 Cells: a Cardiac Muscle Cell Line That Contracts . . . ," Proc Natl Aced Sci USA, vol. 96, No. 6, pp. 2979-2984 (1998).

Davis, D.L. et al., "A GATA-6 Gene Heart-Region-Specific Enhancer Provides a Novel Means to Mark . . . ," Mech Dev, vol. 108, pp. 105-119 (2001).

Demis, S.S. et al., "Parasympathetic Modulation of Sinoatrial Node Pacemaker Activity in Rabbit Heart: a Unifying Model," Am J Physiol, vol. 276, pp. H2221-H2244 (1999).

Doevandans, P.A. et al., "Transcription Factors and the Cardiac Gene Programme," Int J Biochem Cell Biol, vol. 28, pp. 387-403 (1996).

Doevandans, P.A. et al., "Differentiation of Cardiomyocytes in Floating Embryoid Bodies is Comparable to Fetal Cardiomyocytes," J Mol Cell Cardiol, vol. 32, pp. 839-851 (2000).

Edwards, A.V. et al., "Transcription Regulation in the Mouse Atrioventricular Conduction System," Novartis Found Symp, vol. 250, pp. 177-193 (2003).

Evans, M.J. et al., "Establishment in Culture of Pluripotential Cells from Mouse Embryos," Nature, vol. 292, pp. 154-56 (1981).

Gepstein et al., "Somatic Gene and Cell Therapy Strategies for the Treatment of Cardiac Arrythmias," Am J Heart Circ Physiol, vol. 286, pp. H815-H822 (2004).

Ginis, I. et al., "Differences Between Human and Mouse Embryonic Stem Cells," Devel Biol, vol. 269, p. 360 (2004).

Gourdie, R.G. et al., "Development of the Cardiac Pacemaking and Conduction System," Birth Defects Res Part C Embryo Today, vol. 69, pp. 46-57 (2003).

Guyton & Hall, "Capter 10: Rhythmic Excitation of the Heart," Textbook of Medical Physiology 8, pp. 111-117 (1991).

Hamill, O.P. et al., "Improved Patch-Clamp Techniques for High-Resolution Current Recording from Cells and Cell-Free Membrane Patches," Pflugers Arch, vol. 391, p. 85 (1981).

He, C. et al., "The Chicken GATA-6 Locus Contains Multiple Control Regions That Confer Distinct Patterns . . . ," J Biol Chem, vol. 271, p. 28550 (1997).

Hescheler, J. et al., "Embryonic Stem Cells: a Model to Study Structural and Functional Properties in Cardiomyogenesis," Cardiovasc Res, vol. 36, pp. 149-62 (1997).

Hoogaars, W.M. et al., "The Transcriptional Repressor Tbx3 Delineates the Developing Central Conduction System of the Heart," Cardiovasc Res, vol. 62, pp. 489-499 (2004).

Houweling, A.C. et al., "Developmental Pattern of ANF Gene Expression Reveals a Strict Localization of Cardiac Chamber Formation in Chicken," Anat Rec, vol. 266, pp. 93-102 (2002).

Jalife, J. et al., "Connexins and Impulse Propagation in the Mouse Heart," J Cardiovasc Electrophysiol, vol. 10, pp. 1649-1663 (1999).

Karliner, J.S. et al., "Beta-Adrenoceptor and Adenlylate Cyclase Regulation in Cardiac Myocyte Growth," Basic Res Cardiol, vol. 83, pp. 655-663 (1988).

Klug, M.G. et al., "Genetically Selected Cardiomyocytes from Differentiating Embryonic Stem Cells from Stable Intracardiac Grafts," J Clin Invest, vol. 98, pp. 216-224 (1996).

Kondo, R.P. et al., "Development of the Cardiac Conduction System as Delineated by minK-lacZ," J Cardiovasc Electrophysiol, vol. 14, pp. 383-391 (2003).

Kupershmidt, S. et al., "Replacement by Homologous Recombination of the minK Gene . . . ," Circ Res, vol. 84, p. 146 (1999).

Lakatta et al., "Cyclic Variation of Intracellular Calcium," Circ Res, vol. 92, pp. e45-e350 (2003).

Laverriere, A.C. et al., "GATA-4/5/6, a Subfamily of Three Transcription Factors Transcribed in Developing Heart and Gut," J Biol Chem, vol. 269, pp. 23177-23184 (1994).

Lee, M.S. et al., "Stem-Cell Transplantation in Myocardial Infarction: A Status Report," Ann Intern Med, vol. 140, pp. 729-737 (2004).

Li, E. et al., "Targeted Mutation of the DNA Methyltransferase Gene Results in Embryonic Lethality," Cell, vol. 69, p. 915 (1992).

MacKenna, D. et al., "Role of Mechanical Factors in Modulating Cardiac Fibroblast Function and Extracellular Matrix Synthesis," Cardiovasc Res, vol. 46, pp. 257-263 (2000).

Maki, T. et al., "Regulation of Calcium Channel Expression in Neonatal Myocytes by Catecholamines," J Clin Invest, vol. 97, pp. 656-663 (1996).

Maltsev, V.A. et al., "Cardiomyocytes Differentiated in Vitro From Embryonic Stem Cells Developmentally Express Cardiac-Specific Genes . . . ," Circ Res, vol. 75, pp. 233-244 (1994).

Maltsev, V.A. et al., "Embryonic Stem Cells Differentiate in Vitro into Cardiomyocytes Representing Sinusnodal, Atrial and Ventricular Cells Types," Mech Dev, vol. 44, pp. 41-50 (1993).

Martin, G. et al., "Isolation of a Pluripotent Cell Line from Early Mouse Embryos Cultured in Medium Conditioned by . . . ," Proc Nat'l Acad Sci USA, vol. 78, pp. 7634-7638 (1981).

Miake et al., "Biological Pacemaker Created by Gene Transfer," Nature, vol. 419, p. 132 (2002).

Molkentin, J.D. et al., "Direct Activation of a GATA6 Cardiac Enhancer by Nkx2.5 . . . ," Development Biology, vol. 217, p. 301 (2000).

Moorman, A.F. et al., "Development of the Cardiac Conduction System: a Matter of Chamber Development," Novartis Found Symp, vol. 250, pp. 25-43 (2003).

Muller, M. et al., "Selection of Ventricular-like Cardiomyocytes from ES Cells in Vitro," FASEB J, vol. 14, pp. 2540-2548 (2000).

Myers, D.C. et al., "Molecular and Functional Maturation of the Murine Cardiac Conduction System," Trends Cardiovasc Med, vol. 13, pp. 289-295 (2003).

Narita, N. et al., "The Gene for Transcription Factor GATA-6 Resides on Mouse Chromosome 18 and is Expressed in Myocardium and Vascular Smooth Muscle," Genomics, vol. 36, pp. 345-348 (1996).

Nechiporuk, A. et al., "A Proliferation Gradient Between Proximal and Msxb-Expressing Distal Blastema Directs Zebrafish Fin Regeneration," Development, vol. 129, pp. 2607-2617 (2002).

Nichols, J. et al., "Formation of Pluripotent Stem Cells in the Mammalian Embryo Depends on the POU Transcription Factor Oct4," Cell, vol. 95, pp. 379-391 (1998).

Plotnikov, A.N. et al., "Biological Pacemaker Implanted in Canine Left Bundle Branch Provided Ventricular Escape Rhythms . . . ," Circ, vol. 109, pp. 506-512 (2004).

Potapova, I. et al., "Human Mesechymal Stem Cells as a Gene Delivery System to Create Cardiac Pacemakers," Circ Res, vol. 94, p. 952 (2004).

Qu, J. et al., "Expression and Function of Biological Pacemaker in Canine Heart," Circulation, vol. 107, pp. 1106-1109 (2003).

Rentschler, S. et al., "Visualization and Functional Characterization of the Developing Murine Cardiac Conduction System," Development, vol. 128, pp. 1785-1792 (2001).

Sachinidis, A. et al., "Cardiac Specific Differentiation of Mouse Embryonic Stem Cells," Cardiovasc Res, vol. 58, pp. 278-292 (2003).

Sauer, H. et al., "Characteristics of Calcium Sparks in Cardiomyocytes Derived from Embryonic Stem Cells," Am J Physiol Heart Circ Physiol, vol. 281, p. H411 (2001).

Severs, N. J. et al., "Gap Junction Remodeling and Cardiac Arrhythmogenesis: Cause or Coincidence?" J Cell Mol Med, vol. 5, p. 355 (2001).

Stieber, J. The Hyperpolarization-Activated Channel HCN4 is Required for the Generation of Pacemaker Action . . . , Proc Natl Acad Sci USA, vol. 100, p. 15235 (2003).

Suzuki, E. et al., "The Human GATA-6 Gene: Structure, Chromosomal Location, and Regulation of Expression . . . ," Genomics, vol. 15, pp. 283-290 (1996).

Takahashi, T. et al., "Ascorbic Acid Enhances Differentiation of Embryonic Stem Cells into Cardiac Myocytes," Circulation, vol. 107, pp. 1912-1916 (2003).

Takebayashi-Suzuki, K. et al., "Purkinje Fibers of the Avian Heart Express a Myogenic Transcription Factor Program Distinct From . . . ," Dev Biol, vol. 234, pp. 390-401 (2001).

Tamaddon, H.S. et al., "High-Resolution Optical Mapping of the Right Bundle Branch in Connexin40 Knockout Mice Reveal Slow Conduction . . . ," Circ Res, vol. 87, pp. 9829-9836 (2000).

Van Kempen, M.J. et al., "Developmental Changes of Connexin40 and Connexin43 mRNA Distribution Patterns in the Rat Heart," Cardiovasc Res, vol. 32, pp. 886-900 (1996).

Van Kempen, M.J. et al., "Expression of the Electrophysiological System During Murine Embryonic Stem Cell Cardiac Differentiation," Cell Physiol Biochem, vol. 13, pp. 263-270 (2003).

Viatchenko-Karpinski, S. et al., "Intracellular Ca2+ Oscillations Drive Spontaneous Contractions in Carciomyocytes . . . ," Proc Natl Acad Sci USA, vol. 96, p. 8259 (1999).

Wessels, A. et al., "Mouse Models for Cardiac Conduction System Development," Novaris Found Symp, vol. 250, pp. 44-67 (2003).

White, S.M. et al., "Cardiac Physiology at the Cellular Level," Am J Physiol Heart Circ Physiol, vol. 286, pp. H823-H829 (2004).

Wobus, A.M. et al., "Development of Cardiomyocytes Expressing Cardiac-Specific Genes, Action Potentials, and Ionic Channels . . . ," Ann N Y Acad Sci, vol. 752, pp. 460-469 (1995).

Wu, J. et al., "Morphological and Membrane Characteristics of Spider and Spindle Cells Isolated from Rabbit Sinus Node," Am J Physiol Heart Circ Physiol, vol. 280, p. H1232 (2001).

Wu, J. et al., "Transmural Reentry During Acute Global Ischemia and Reperfusion in Canine Ventricular Muscle," Am J Phsiol Heart Circ Physiol, vol. 280, pp. H2717-H2725 (2001).

Xavier-Neto, J. et al., "A Retinoic Acid-Inducing Transgenic Marker of Sino-Artial Development in the Mouse Heart," Development, vol. 126, pp. 2677-2687 (1999).

Zhang, Y.M. et al., "Characterization and Regulation of T-type Ca2+ Channels in Embryonic Stem Cell-Derived Cardiomyocytes," Am J Physiol Heart Circ Physiol, vol. 285, pp. H2770-H2779 (2003).

* cited by examiner

Figure 3 A - F
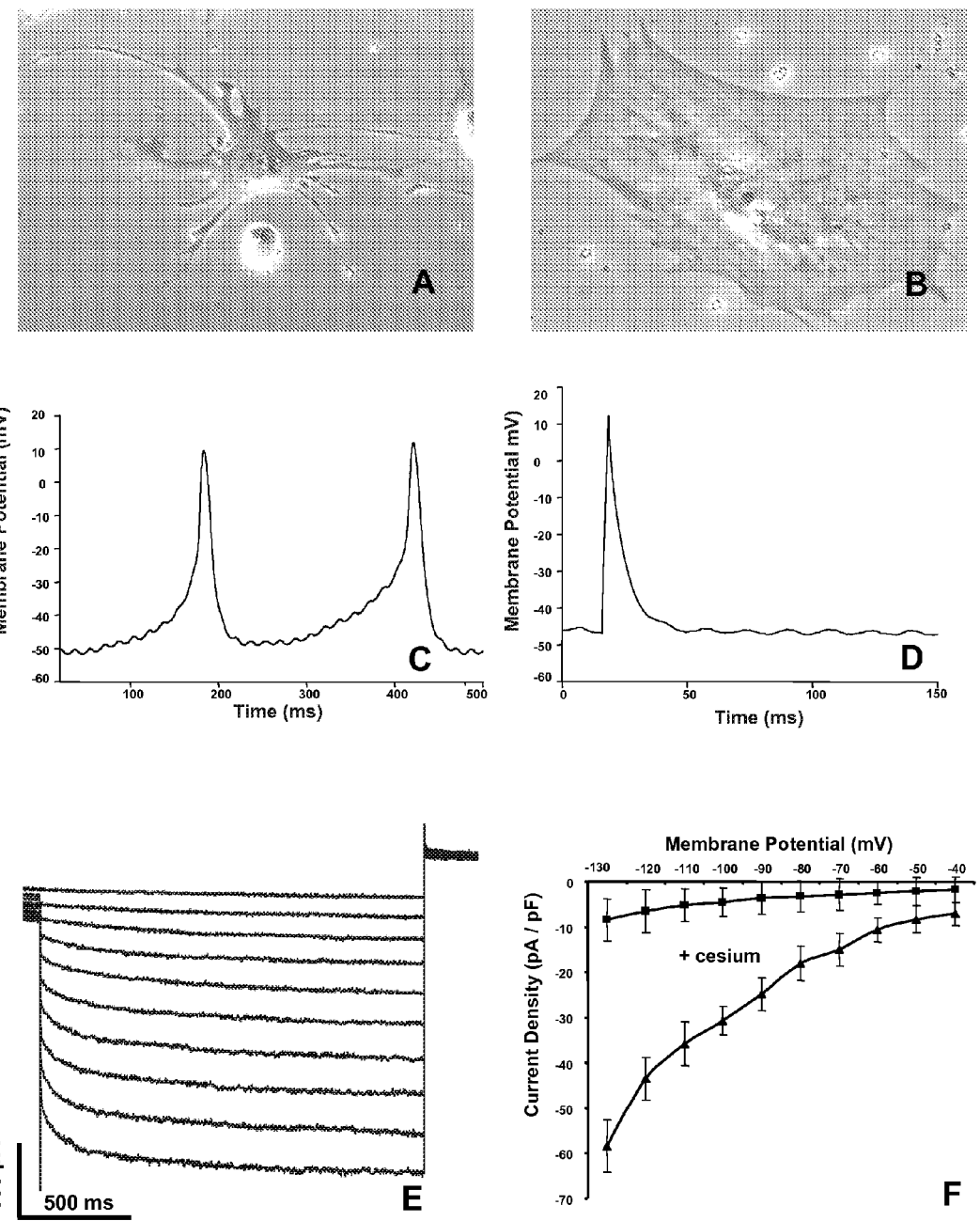

Figure 4
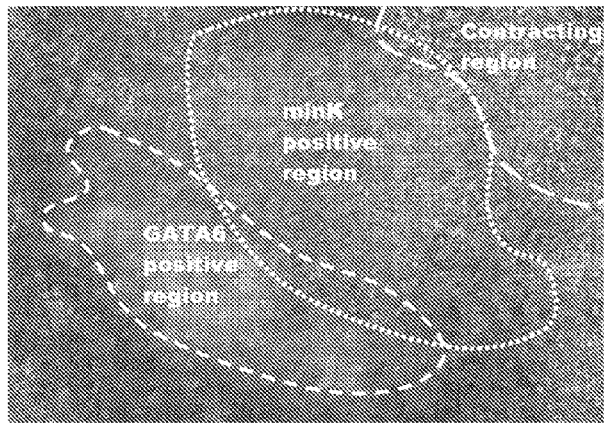
Figure 5
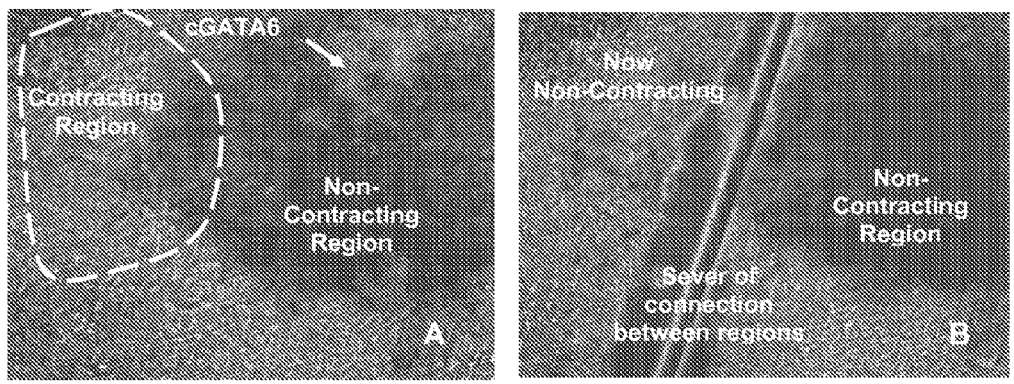
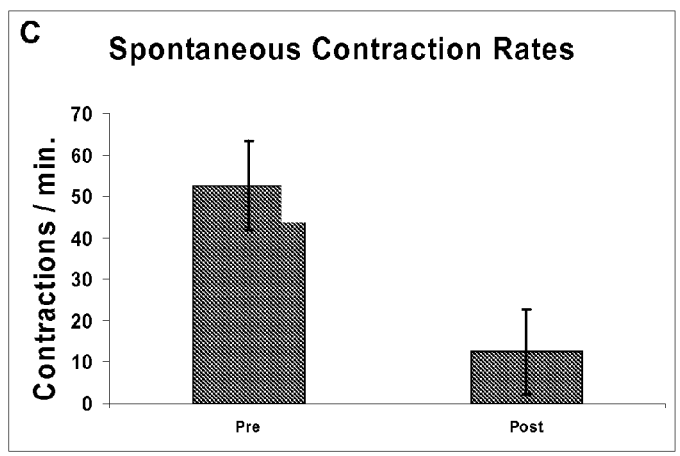

Figure 6

[-1.5/0.0] FRAGMENT OF THE CHICKEN GATA6 PROMOTER/Enhancer

```
-1469 GAGCTCCCGCTGCCCGCGCGATAACGCCGGCCCCGACGTCGCAGCGCGGGGGGTGGCGGC
-1409 GATAACAGAGTATTTGAAGGCGCTGGGATAAGGAGCGGAGGGACGCGCGGGCGGCACGTC
-1349 GGCGCTCGGGGCGCTGCGTTATCGGCCCGGCCCCAAACGCTCCCCGCGCCGCTCGGGTAC
-1289 ATCGCGTTACATAAACACCGCCCGGGGAGAGCGCGACGGTCCCCAAAGTGACCCCTCGCA
-1229 CCCGGCCCGGCCCTCCCCGAGATGAGGTGCGCCCGCAGAGGAGGGGTTTGGGGGTTGGGG
-1169 GGGAGGTTGCCCTAAGGGATCGCAACGCCCGGCTGTGGGGTTTGGGGTTGGTTTGTATGG
-1109 GGGCTCACCGCTACGTCAGAAGAGCGCACGGAGGAGCTGGCGGCAGCGGGGCGGCGGGGG
-1049 GCACAGCCGTGCCGGGGGTCGGCCAGCGGGGCTCCGAAGGGAGCGTGGGGCCGGCGGCGT
 -989 TTAGGGGCGGGGATCGGTGTGTGTGTGTGGGGGGGGGGGGGGGGGAAGGGGGGAGGCGGC
 -929 GTCTGTATCACCCCCGGGGCTCCCCCGCAGGTAACGAACACGGAGGGAGAAAGAAAAAGC
 -869 GTTTTACGTGGCACAGTCGTATGGGAGTGAGCGCGGGGCGTTGAGAGACAGCGGATCGCT
 -809 GCTTCGAGTAGGTTATTTTCCACGCGTTATCACGCCCGTTAACAAACATCGAAAGGTAAA
 -749 AATAACGACGGAGCGCAAGGAAATGAAATCAAATGCACGTGATTATTTTTAGGAAGATAA
 -689 AATAAAACGCAAATAAAACAAAAAGCCGGGAGGAGAACATCAGTGCCCGCACAGAGCCCG
 -629 GAGGAAAGCCACAATCCAACGGAGGAACGTTCCCACTCGCTCCCCCCATCCCGGCCCCCC
 -569 CAGGTTCTCGCCGTAGGGGCCCCCCCAGTTCACCCCCCCCCCCTTCCCCGCCCTTCGCGG
 -509 AGCGACGCCGACAGATCCGCAGGCGATAACCTCGGGGCAACGCCGTTATTTTAATTTTAC
 -449 AGTCACTTTAGCGCTATCAGTTTGTACACAGCTGAGATAAGAGGATCGAAGGGTGAGGGG
 -389 GGGGGGGAGGGGGAGGTAGAGGGGGAAAAAAGAAGAAGGAGAAAGAAGCGGCGGAGAAA
 -329 TGCGCACGCCGCCGGCTCGCACACGGCTTTGGCCTCACCTGACGGCCGGGGAGGAGCGCG
 -269 CGTTCGCCCTCGCAGCGCTCAGACGCTAAGGAGCAGAACGAAGGGTTAACGGCGGCGACA
 -209 CCGCCGAGCGCGGCCCCCCCCGCCCCCCTCCTCCCCTGCCCGGCCCCGAGCGCCGCGGTG
 -149 CCCCCCCGGCCGCCCGCCCGCGGCTCCCGCGGAGCCGCTGTTTGCTCAGCGCCCGGAGCC
  -89 CAATCAGGGCCGCTCCGCCTGCACTTTCCCGGCCCGGCGGCGAGAGGCGCCTCCTCTCTC
                                  +1
  -29 CCATTTATACGCCGCCGCCGCAGCCGCT|GCCCCTCGGCGCTGGATCC    SEQ ID NO:1
                                            → *START OF TRANSCRIPTION*
```

[-4.0/.2 kb] Fragment of the Murine MinK Enhancer

*EcoR1 site*

```
   1 gaattcactt atggacggaa ccatggatta agtcaaagca ttcataatct aatcacctct
  61 ggaaagattc tcccagacat acccagaggt gtgccttaca agtattctag tggtctctta
 121 gtcctgtcaa gtgggtagcc aagaccaacc agccatatct gtactcagga ccactaactg
 181 tcaaccagcg catgccgtgt tccatgcttg gtcggcgacc aaacagcctg gaaatgtggg
 241 tgttgggttt tcctgttttt ccgagaggaa aggacacagc caagagaggc tgaggaacat
 301 ttctaggatc acgtgtccat gaagttacag agccggaatc caaagtggga ggtgggaggc
 361 caaagtctga gcatgttctg ccccttttaag agtgggtttg gaggctggag agatgggtca
 421 gcggttaaga acaccgactg ctctcccaga ggtcctgagt tcaattccca gcaatgacat
 481 ggtggctctc aaccatctgt aatgggatct gaagctctct tctggtgtgt ctgaagagag
 541 caatggtata ttcatataca taaaataaat aaataaatct taaaaaaga cattaaaaaa
 601 aaagagcagg tttgggtgag agacaactaa agctctgaag ctagcttgat ggtctctttt
 661 aatgaaaata agcaggtttt agagagccag gccctgtgtg gggacagta ttacgttttg
 721 attataaatg tttactaaat gtcaataaa tgttcctggg tagctcttgt gctgctgtgg
 781 accaggcacc agctcagatg agtagagatg gagtctaaag atcttgcctg ggatgaagtt
 841 ggcagcgtca atcagaatga tgctaaccca gccctatgga ccaaagaagg tctcaggaac
 901 aaagtgtgag ctgggggtc tcattctcca agtatgagta acacattgtg gagccggtct
 961 gaactggaaa tgggcaaaga cacgaggaca agtggaaagt tcagtgaagg gccagaaaga
1021 ctggaggcat ggctcctgag gacagtgaca gcaatggagg aatggagctg tgatcctcaa
1081 actcagagcc catccacagc tgtgctctgg acaggccatt tccttctgaa gataacaagg
1141 gacagatgaa aaccctcact tggggctgct atagtaagat ttgctgcagt tttcatgtgg
1201 aggccatggc tgttgagctc agcgagacgc aggagggtg ctgatgggat gcagttggag
1261 ttctgtgtcg gagcggcctg ggaatggcca aagggaaatt ttgatgagca gtgtcccatg
1321 gctcttgtgc tgagacagga gagctggggt caaggccatg tgtatgattc tgaaggaaca
1381 ggtgtggtca ccggggcaag gctggcagga gagggagagc aggggagtgg gtagggcac
1441 taacagtcaa cggtggcatg tagggcaagg aggcctcaga aagcagaaag catcttcacc
1501 tggggctggg ttcaggttca tctttaaaaa caatttgttg agccaggcgt ggtggcgcac
1561 acctttaatc tcagcacttg ggaggcagag gcaggcggat ttctgagttc gaagccagcc
1621 tggtctacag agtgagttcc aggacagcca gggctataca gagaaaccct gtcttgaaga
1681 aaaaaaaac aaaacgattt gtttattctt attttaagtg gactggtgtt ttgcctgcag
1741 tgtgaaggtg tcaatcactt gaagctgtac tacaggcagt gtgagctgcc actcggctgc
1801 tgggaattga actcgggtcc tttggaagag catccaatgc tcttaacccc tgaaccatct
1861 ctccaggccc tcaggctcat ttttaaatta agtcagttct acaagaagt agctataggt
1921 ctaacccaga gtgagctgag agttctgggg ttgatggttg tccagagat gatgttggtc
1981 gatgtcacag tccccactct agctggggga tgctgagctg ccatgatgta tgttaggctt
2041 tcttttcatg gtgattctgg ccagaaactg tgtcccaagc atgcctttgc ctctagctac
2101 aaaagtcact cagggggacct catggcata ttctacttgg ctgccagaag atgcctagga
2161 gaagaggttg gaccacccca aacctggcaa actcctagcg gtcattttg aattgaacta
2221 cacatctcta ggagagagga gtagaaggtg atatttaccc tacacccacc ccaaaggaat
2281 ataagttttc actcatcagt gatctgatgg tcacctaggg gtggggttc ttaggacacg
2341 caaatatctc gacagagtcc tacagtcact cggagacact tctcacagtg accaagcctg
2401 ggtgttcaga tgagaaatca tcctgtcagg agtgatgtgt ttgttcttca ggggcccatc
2461 agtcactcac tggaggaggt gatcggagaa gggaggttag catgctgagc acctacctac
2521 caggtcctca gattggagtg ttggaaactc agcacacctt ccacggctgc tacattatag
2581 tgtttgtctt ccactcaggg agctcagctg ccctaagaga cgtccatgga gaaacagctc
2641 ccccaacccc tagatccaag taccgtgtgc ctgcatggtt tataaggaac aaagctttgt
```

Figure 7A

```
2701 ttgtgtcaca gttctgaaga cgtccaacag tgcggtatgg tcacgtgtca gaacacttaa
2761 agcgccttgt actataccoc gatgtggcaa gacagagcaa ggtagccaaa gatagctcat
2821 tatatccatg aacgagtgac tggataataa aggccatctg tcaataacac actcatctat
2881 aaatggattc atctattcac aagggccagc atccttgtga cacaatcacc ttctagtagt
2941 ctataaatgg attcatttat tcacaagggc cagcatcctt gtgacacaat caccttcagt
3001 agtctttcca acatgtgggc ttttggggac acattccac tatagcaacc acccactgca
3061 cattccatcc aaaggtgccc tgacagcccc ttcggctgaa tggttatggt aaccactgta
3121 gttccttgtc agttgctgtg ataaacgtgg cgaacacaaa tggcctatgg aagaaagagt
3181 tctcttgact tacggtttta gagagagaga gagagagaga gagagagaga gagttcataa
3241 tggctgggaa gggaggtgtg tcggctgcca gtcaggacag gaaactgaga gctcacatct
3301 tcatctgcat acaggaaaca gagaaccgga agtggccaag tctgtaagcc cccaaaaccc
3361 tccccaaatt ctgtgtttcc tccaccaagc cgtcacatct taaaagttct gcaacttcat
3421 tctgcagacc caaactcaca gggatcctcc tgcctctgtt ttttgtttgt ttgtttgttt
3481 tgttttttc tggtgatatt tttatcttgt aaaggttttt aaattacctt aatttatttt
3541 gtgtttgtgc atatgtatgt gtatgttggg ggggcacac atgtggaggt cagaggtcag
3601 tttacaggca tcagttctct cgtcccacca cgtgggaggc agggatggaa ctcagggcgc
3661 caggtttaac cagcactttc acccactgat ctatttgcca ggccatctgc tttgtttgtt
3721 tacggagtga gtggccagca tagttttctt ttgtaggggg agtgggcaga gagagaaacg
3781 agtgtttgac aggggttgag tgtaaggaaa tgcacgcgca agcagcaata ttaatgggcc
3841 gtaaagtcaa tgataatggg aagaggaaag agagccaatg agatacacgg ctctgtatcg
3901 ttatgacaca cgacatggca atgtgaacta tgacgatgag actcatccca atggccgcct
3961 gccagagagc gggaggacgg ctgattgagt catcaactga ttgacagacc agtgagagga
4021 tgtctgctca tgcctgccac ccaagacgct aaagaatcgt gtgcatgggg tgggaggtag
4081 ccaatcaggc ccagaatcgt gtgctggaat tagccaatca ggctaagaac tgtgtgcacg
4141 ggtgggaggt agccaatcat gcttttgat tctaagttgc cttttccttt cagGAGTTTT
location of oligo based Xba I site insert  minK start
4201 gctctgcatc aggggaacct tgacgcccag gATGAGCCTG CCCAATTCCA CGACTGTTCT
4261 GCCCTTTCTG GCCAGGCTGT GGCAGGAGAC AGCTGAACAG GGCGGCAACG TGTCCGGCCT
4321 GGCTCGTAAG TCTCAGCTCC GAGATGACAG CAAGCTAGAG GCGCTCTACA TCCTCATGGT
4381 GCTGGGCTTC TTCGGCTTCT TCACCCTGGG CATCATGCTG AGTTACATCC GATCCAAGAA
4441 GCTGGAGCAC TCCCACGACC CTTTCAACGT GTACATCGAG TCAGATGCCT GGCAGGAGAA
4501 AGGCAAGGCC GTCTTCCAGG CCCGTGTCCT GGAGAGCTTC AGAGCTTGCT ATGTCATTGA
4561 AAACCAGGCG GCCGTAGAGC AGCCTGCCAC ACACCTTCCT GAACTGAAGC CATTGTCGTG
4621 A  . . .    SEQ ID NO:2
```

Figure 7B

Figure 8 A - F
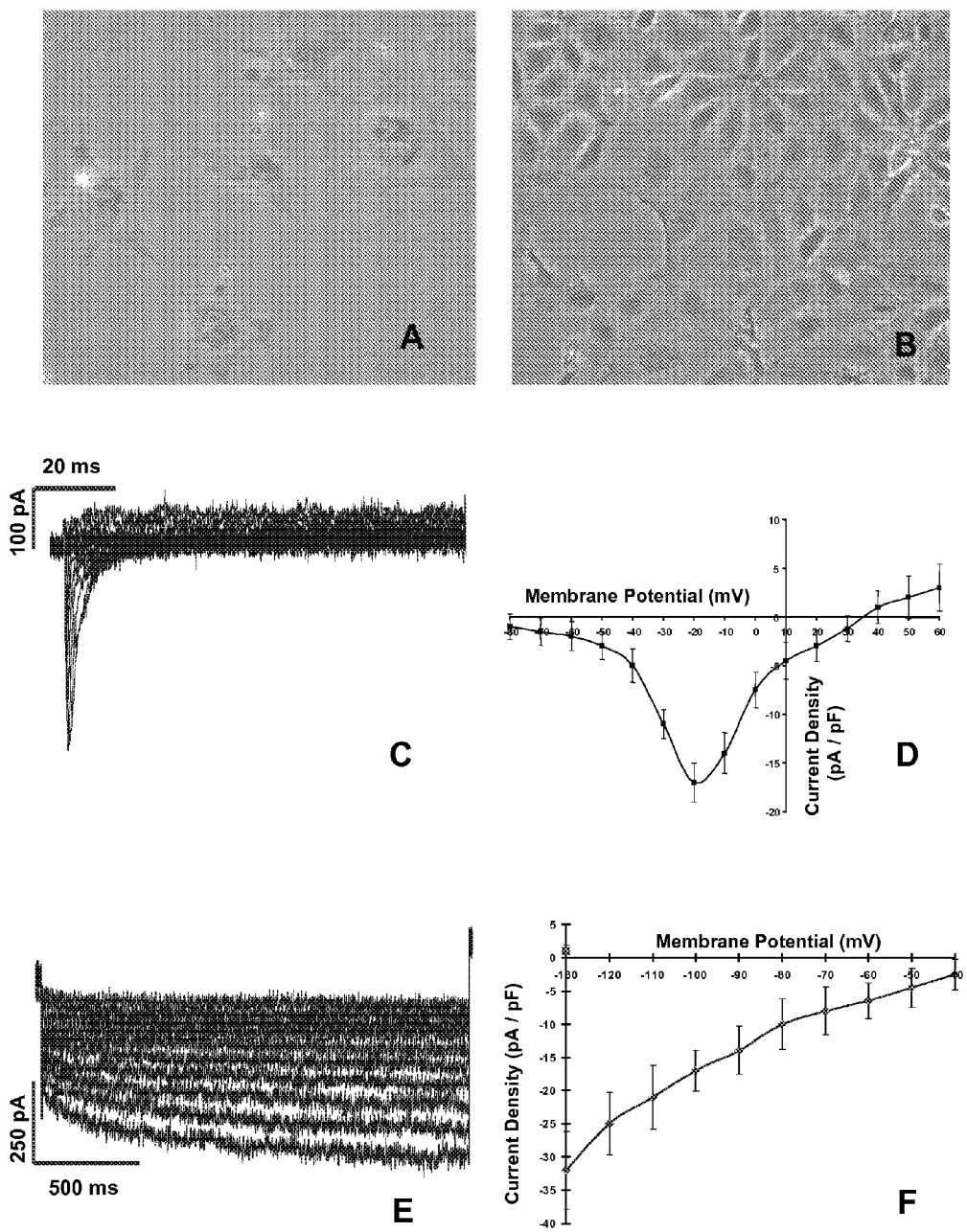

SEQUENCE LISTING

```
<160> NUMBER OF SEQ ID NOS: 72

<210> SEQ ID NO 1
<211> LENGTH: 1488
<212> TYPE: DNA
<213> ORGANISM: Gallus sp.

<400> SEQUENCE: 1
gagctcccgc tgcccgcgcg ataacgccgg ccccgacgtc gcagcgcggg gggtggcggc      60
gataacagag tatttgaagg cgctgggata aggagcggag ggacgcgcgg gcggcacgtc     120
ggcgctcggg gcgctgcgtt atcggcccgg ccccaaacgc tccccgcgcc gctcgggtac     180
atcgcgttac ataaacaccg cccggggaga gcgcgacggt ccccaaagtg accctcgca      240 cccggcccgg ccctccccga gatgaggtgc gcccgcagag gaggggtttg gggttgggg      300 gggaggttgc cctaagggat cgcaacgccc ggctgtgggg tttggggttg gtttgtatgg     360
```

```
gggctcaccg ctacgtcaga agagcgcacg gaggagctgg cggcagcggg gcggcggggg    420
gcacagccgt gccgggggtc ggccagcggg gctccgaagg gagcgtgggg ccggcggcgt    480
ttaggggcgg ggatcggtgt gtgtgtgtgg ggggggggggg ggggggaaggg gggaggcggc   540 gtctgtatca cccccgggc tcccccgcag gtaacgaaca cggagggaga aagaaaaagc    600
gttttacgtg gcacagtcgt atgggagtga gcgcggggcg ttgagagaca gcggatcgct    660
gcttcgagta ggttatttc cacgcgttat cacgcccgtt aacaaacatc gaaaggtaaa    720
aataacgacg gagcgcaagg aaatgaaatc aaatgcacgt gattattttt aggaagataa    780
aataaaacgc aaataaaaca aaaagccggg aggagaacat cagtgcccgc acagagcccg    840
gaggaaagcc acaatccaac ggaggaacgt tcccactcgc tcccccatc ccggcccccc    900 caggttctcg ccgtagggc cccccagtt cacccccccc ccttcccg ccttcgcgg        960 agcgacgccg acagatccgc aggcgataac ctcggggcaa cgccgttatt ttaatttac    1020 agtcacttta gcgctatcag tttgtacaca gctgagataa gaggatcgaa gggtgagggg    1080 ggggggggagg gggaggtaga gggggaaaa aagaagaagg agaagaagc ggcggagaaa    1140 tgcgcacgcc gccggctcgc acacggcttt ggcctcacct gacggccggg gaggagcgcg    1200
cgttcgccct cgcagcgctc agacgctaag gagcagaacg aagggttaac ggcggcgaca    1260
ccgccgagcg cggccccccc cgccccccctc ctccccctgcc cggccccgag cgccgcggtg  1320 ccccccggc cgcccgcccg cggctcccgc ggagccgctg tttgctcagc gcccggagcc    1380
caatcagggc cgctccgcct gcactttccc ggcccggcgg cgagaggcgc ctcctctctc    1440
ccatttatac gccgcccgcc gcagccgctg cccctcggcg ctggatcc              1488

<210> SEQ ID NO 2
<211> LENGTH: 4621
<212> TYPE: DNA
<213> ORGANISM: murine

<400> SEQUENCE: 2
gaattcactt atggacggaa ccatggatta agtcaaagca ttcataatct aatcacctct     60
ggaaagattc tcccagacat acccagaggt gtgccttaca agtattctag tggtctcttca   120 gtcctgtcaa gtgggtagcc aagaccaacc agccatatct gtactcagga ccactaactg   180
tcaaccagcg catgccgtgt tccatgcttg gtcggcgacc aaacagcctg gaaatgtggg   240
tgttgggttt tcctgttta ccgagaggaa aggacacagc caagagaggc tgaggaacat   300
ttctaggatc acgtgtccat gaagttacag agccggaatc caaagtggga ggtgggaggc   360
caaagtctga gcatgttctg cccctttaag agtgggtttg gaggctggag agatgggtca   420
gcggttaaga acaccgactg ctctcccaga ggtcctgagt tcaattccca gcaatgacat   480
ggtggctctc aaccatctgt aatgggatct gaagctctct tctggtgtgt ctgaagagag   540
caatggtata ttcatataca taaaataaat aaataaatct taaaaaaaga cattaaaaaa   600
aaagagcagg tttgggtgag agacaactaa agctctgaag ctagcttgat ggtctctttt   660
aatgaaaata agcaggtttt agagagccag gccctgtgtg ggggacagta ttacgttttg   720
attataaatg tttactaaat gctcaataaa tgttcctggg tagctcttgt gctgctgtgg   780
accaggcacc agctcagatg agtagagatg gagtctaaag atcttgcctg ggatgaagtt   840
ggcagcgtca atcagaatga tgctaaccca gccctatgga ccaaagaagg tctcaggaac   900
aaagtgtgag ctggggggtc tcattctcca gtatgagta acacattgtg gagccggtct    960
gaactggaaa tgggcaaaga cacgaggaca agtggaaagt tcagtgaagg gccagaaaga  1020
```

```
ctggaggcat ggctcctgag gacagtgaca gcaatggagg aatggagctg tgatcctcaa    1080
actcagagcc catccacagc tgtgctctgg acaggccatt tccttctgaa gataacaagg    1140
gacagatgaa aaccctcact tggggctgct atagtaagat ttgctgcagt tttcatgtgg    1200
aggccatggc tgttgagctc agcgagacgc aggaggggtg ctgatgggat gcagttggag    1260
ttctgtgtcg gagcggcctg ggaatggcca agggaaatt ttgatgagca gtgtcccatg     1320
gctcttgtgc tgagacagga gagctggggt caaggccatg tgtatgattc tgaaggaaca    1380
ggtgtggtca ccggggcaag gctggcagga gagggagagc aggggagtgg gtaggggcac    1440
taacagtcaa cggtggcatg tagggcaagg aggcctcaga aagcagaaag catcttcacc    1500
tggggctggg ttcaggttca tctttaaaaa caatttgttg agccaggcgt ggtggcgcac    1560
acctttaatc tcagcacttg ggaggcagag gcaggcggat ttctgagttc gaagccagcc    1620
tggtctacag agtgagttcc aggacagcca gggctataca gagaaaccct gtcttgaaga    1680
aaaaaaaaac aaaacgattt gtttattctt attttaagtg gactggtgtt ttgcctgcag    1740
tgtgaaggtg tcaatcactt gaagctgtac tacaggcagt gtgagctgcc actcggctgc    1800
tgggaattga actcgggtcc tttggaagag catccaatgc tcttaaccc tgaaccatct     1860 ctccaggccc tcaggctcat ttttaaatta agtcagttct acaaagaagt agctataggt    1920
ctaacccaga gtgagctgag agttctgggg ttgatggttg tcccagagat gatgttggtc    1980
gatgtcacag tccccactct agctggggga tgctgagctg ccatgatgta tgttaggctt    2040
tcttttcatg gtgattctgg ccagaaactg tgtcccaagc atgcctttgc ctctagctac    2100
aaaagtcact caggggacct catgggcata ttctacttgg ctgccagaag atgcctagga    2160
gaagaggttg gaccacccca aacctggcaa actcctagcg gtcattttg aattgaacta     2220 cacatctcta ggagagagga gtagaaggtg atatttaccc tacacccacc ccaaaggaat    2280
ataagttttc actcatcagt gatctgatgg tcacctaggg gtggggttc ttaggacacg     2340 caaaatatct gacagagtcc tacagtcact cggagacact tctcacagtg accaagcctg    2400
ggtgttcaga tgagaaatca tcctgtcagg agtgatgtgt tgttcttca ggggcccatc     2460 agtcactcac tggaggaggt gatcggagaa gggaggttag catgctgagc acctacctac    2520
caggtcctca gattggagtg ttggaaactc agcacacctt ccacggctgc tacattatag    2580
tgtttgtctt ccactcaggg agctcagctg ccctaagaga cgtccatgga gaaacagctc    2640
ccccaacccc tagatccaag taccgtgtgc ctgcatggtt tataaggaac aaagctttgt    2700
ttgtgtcaca gttctgaaga cgtccaacag tgcggtatgg tcacgtgtca gaacacttaa    2760
agcgccttgt actataccc gatgtggcaa gacagagcaa ggtagccaaa gatagctcat     2820
tatatccatg aacgagtgac tggataataa aggccatctg tcaataacac actcatctat    2880
aaatggattc atctattcac aagggccagc atccttgtga cacaatcacc ttctagtagt    2940
ctataaatgg attcatttat tcacaagggc cagcatcctt gtgacacaat caccttcagt    3000
agtctttcca acatgtgggc ttttggggac acattcccac tatagcaacc cccactgca     3060 cattccatcc aaaggtgccc tgacagcccc ttcggctgaa tggttatggt aaccactgta    3120
gttccttgtc agttgctgtg ataaacgtgg cgaacacaaa tggcctatgg aagaaagagt    3180
tctcttgact tacggtttta gagagagaga gagagagaga gagagagaga gagttcataa    3240
tggctgggaa gggaggtgtg tcggctgcca gtcaggacag gaaactgaga gctcacatct    3300
tcatctgcat acaggaaaca gagaaccgga agtggccaag tctgtaagcc cccaaaaccc    3360
tccccaaatt ctgtgtttcc tccaccaagc cgtcacatct taaaagttct gcaacttcat    3420
```

```
tctgcagacc caaactcaca gggatcctcc tgcctctgtt ttttgtttgt ttgtttgttt    3480 tgttttttc tggtgatatt tttatcttgt aaaggttttt aaattacctt aatttatttt    3540
gtgtttgtgc atatgtatgt gtatgttggg ggggcacac atgtggaggt cagaggtcag    3600
tttacaggca tcagttctct cgtcccacca cgtgggaggc agggatggaa ctcagggcgc    3660
caggtttaac cagcactttc acccactgat ctatttgcca ggccatctgc tttgtttgtt    3720
tacggagtga gtggccagca tagttttctt ttgtaggggg agtgggcaga gagagaaacg    3780
agtgtttgac aggggttgag tgtaaggaaa tgcacgcgca agcagcaata ttaatgggcc    3840
gtaaagtcaa tgataatggg aagaggaaag agagccaatg agatacacgg ctctgtatcg    3900
ttatgacaca cgacatggca atgtgaacta tgacgatgag actcatccca atggccgcct    3960
gccagagagc gggaggacgg ctgattgagt catcaactga ttgacagacc agtgagagga    4020
tgtctgctca tgcctgccac ccaagacgct aaagaatcgt gtgcatgggg tgggaggtag    4080
ccaatcaggc ccagaatcgt gtgctggaat tagccaatca ggctaagaac tgtgtgcacg    4140
ggtgggaggt agccaatcat gcttttgat tctaagttgc cttttccttt caggagtttt    4200
gctctgcatc aggggaacct tgacgcccag gatgagcctg cccaattcca cgactgttct    4260 gcccttctg gccaggctgt ggcaggagac agctgaacag ggcggcaacg tgtccggcct    4320
ggctcgtaag tctcagctcc gagatgacag caagctagag gcgctctaca tcctcatggt    4380
gctgggcttc ttcggcttct tcaccctggg catcatgctg agttacatcc gatccaagaa    4440
gctggagcac tcccacgacc ctttcaacgt gtacatcgag tcagatgcct ggcaggagaa    4500
aggcaaggcc gtcttccagg cccgtgtcct ggagagcttc agagcttgct atgtcattga    4560
aaaccaggcg gccgtagagc agcctgccac acaccttcct gaactgaagc cattgtcgtg    4620
a                                                                   4621
```

```
<210> SEQ ID NO 3
<211> LENGTH: 20
<212> TYPE: DNA
<213> ORGANISM: murine

<400> SEQUENCE: 3
tcaagaaggt ggtgaagcag                                                 20

<210> SEQ ID NO 4
<211> LENGTH: 20
<212> TYPE: DNA
<213> ORGANISM: murine

<400> SEQUENCE: 4
ccctgttgct gctgtagccg                                                 20

<210> SEQ ID NO 5
<211> LENGTH: 20
<212> TYPE: DNA
<213> ORGANISM: murine

<400> SEQUENCE: 5
tgaatgaact gcaggacgag                                                 20

<210> SEQ ID NO 6
<211> LENGTH: 20
<212> TYPE: DNA
<213> ORGANISM: Murine

<400> SEQUENCE: 6
```
atactttctc ggcaggagca                    20

<210> SEQ ID NO 7

<400> SEQUENCE: 7

000

<210> SEQ ID NO 8

<400> SEQUENCE: 8

000

<210> SEQ ID NO 9
<211> LENGTH: 20
<212> TYPE: DNA
<213> ORGANISM: murine

<400> SEQUENCE: 9
ccgggctgtc atctcactat                    20

<210> SEQ ID NO 10
<211> LENGTH: 20
<212> TYPE: DNA
<213> ORGANISM: murine

<400> SEQUENCE: 10
gcctgcgatg tctgagtgac                    20

<210> SEQ ID NO 11
<211> LENGTH: 20
<212> TYPE: DNA
<213> ORGANISM: murine

<400> SEQUENCE: 11
gccaactgtc acaccacaac                    20

<210> SEQ ID NO 12
<211> LENGTH: 20
<212> TYPE: DNA
<213> ORGANISM: murine

<400> SEQUENCE: 12
tgttaccgga gcaagctttt                    20

<210> SEQ ID NO 13
<211> LENGTH: 20
<212> TYPE: DNA
<213> ORGANISM: murine

<400> SEQUENCE: 13
ctccacctcg gctctgtaac                    20

<210> SEQ ID NO 14
<211> LENGTH: 20
<212> TYPE: DNA
<213> ORGANISM: murine

<400> SEQUENCE: 14
cttgatgctg aggctttgag                    20

<210> SEQ ID NO 15
<211> LENGTH: 20
<212> TYPE: DNA

-continued

<213> ORGANISM: murine

<400> SEQUENCE: 15
aggaaacaca agaccaaccg                                            20

<210> SEQ ID NO 16
<211> LENGTH: 20
<212> TYPE: DNA
<213> ORGANISM: murine

<400> SEQUENCE: 16
gcagccattt tcagcttttc                                            20

<210> SEQ ID NO 17
<211> LENGTH: 20
<212> TYPE: DNA
<213> ORGANISM: murine

<400> SEQUENCE: 17
cacgactgct ttcttcacca                                            20

<210> SEQ ID NO 18
<211> LENGTH: 19
<212> TYPE: DNA
<213> ORGANISM: murine

<400> SEQUENCE: 18
atatcccagt tcctgggtc                                             19

<210> SEQ ID NO 19
<211> LENGTH: 20
<212> TYPE: DNA
<213> ORGANISM: murine

<400> SEQUENCE: 19
ttaggagaag ggcgatgact                                            20

<210> SEQ ID NO 20
<211> LENGTH: 20
<212> TYPE: DNA
<213> ORGANISM: murine

<400> SEQUENCE: 20
aggtccgaga caccaggcta                                            20

<210> SEQ ID NO 21
<211> LENGTH: 20
<212> TYPE: DNA
<213> ORGANISM: murine

<400> SEQUENCE: 21
gggtcatctg ctagcctcag                                            20

<210> SEQ ID NO 22
<211> LENGTH: 20
<212> TYPE: DNA
<213> ORGANISM: murine

<400> SEQUENCE: 22
tatgctggga gaggtggaac                                            20

<210> SEQ ID NO 23
<211> LENGTH: 20
<212> TYPE: DNA

<213> ORGANISM: murine

<400> SEQUENCE: 23
aggagcgtgt ctgtcaggtt                              20

<210> SEQ ID NO 24
<211> LENGTH: 20
<212> TYPE: DNA
<213> ORGANISM: murine

<400> SEQUENCE: 24
gccattacct ccccaatttt                              20

<210> SEQ ID NO 25
<211> LENGTH: 20
<212> TYPE: DNA
<213> ORGANISM: murine

<400> SEQUENCE: 25
atggtccgta actggcaaag                              20

<210> SEQ ID NO 26
<211> LENGTH: 19
<212> TYPE: DNA
<213> ORGANISM: murine

<400> SEQUENCE: 26
ttcgtctgct ttcacgatg                               19

<210> SEQ ID NO 27
<211> LENGTH: 20
<212> TYPE: DNA
<213> ORGANISM: murine

<400> SEQUENCE: 27
tctgagatgt ctctctctta                              20

<210> SEQ ID NO 28
<211> LENGTH: 21
<212> TYPE: DNA
<213> ORGANISM: murine

<400> SEQUENCE: 28
cgtacaatga ctgatgagag a                            21

<210> SEQ ID NO 29
<211> LENGTH: 20
<212> TYPE: DNA
<213> ORGANISM: murine

<400> SEQUENCE: 29
gacaatcgac aatcgtgctg                              20

<210> SEQ ID NO 30
<211> LENGTH: 21
<212> TYPE: DNA
<213> ORGANISM: murine

<400> SEQUENCE: 30
tccacagggc tttgtttgag t                            21

<210> SEQ ID NO 31
<211> LENGTH: 20
<212> TYPE: DNA

<213> ORGANISM: murine

<400> SEQUENCE: 31
gaagatgcac gacgaggaat                                        20

<210> SEQ ID NO 32
<211> LENGTH: 21
<212> TYPE: DNA
<213> ORGANISM: murine

<400> SEQUENCE: 32
cgaacgttta tgtttattgt a                                      21

<210> SEQ ID NO 33
<211> LENGTH: 20
<212> TYPE: DNA
<213> ORGANISM: murine

<400> SEQUENCE: 33
gggcctgaat gaggagtaga                                        20

<210> SEQ ID NO 34
<211> LENGTH: 21
<212> TYPE: DNA
<213> ORGANISM: murine

<400> SEQUENCE: 34
gttgcaaagg ctccaggtct c                                      21

<210> SEQ ID NO 35
<211> LENGTH: 20
<212> TYPE: DNA
<213> ORGANISM: murine

<400> SEQUENCE: 35
ctcgggaggg taagtgttcc                                        20

<210> SEQ ID NO 36
<211> LENGTH: 21
<212> TYPE: DNA
<213> ORGANISM: murine

<400> SEQUENCE: 36
catgcggaag gcactcaggc g                                      21

<210> SEQ ID NO 37
<211> LENGTH: 21
<212> TYPE: DNA
<213> ORGANISM: murine

<400> SEQUENCE: 37
gagaccattc tcaacgcatt c                                      21

<210> SEQ ID NO 38
<211> LENGTH: 21
<212> TYPE: DNA
<213> ORGANISM: murine

<400> SEQUENCE: 38
ggaaaggctg cgaacatctt c                                      21

<210> SEQ ID NO 39
<211> LENGTH: 20
<212> TYPE: DNA

<213> ORGANISM: murine

<400> SEQUENCE: 39
gtgaagatgg ccttggatgt          20

<210> SEQ ID NO 40
<211> LENGTH: 21
<212> TYPE: DNA
<213> ORGANISM: murine

<400> SEQUENCE: 40
tggacttcag aaccccttg g          21

<210> SEQ ID NO 41
<211> LENGTH: 20
<212> TYPE: DNA
<213> ORGANISM: murine

<400> SEQUENCE: 41
tctttgcttc tgccctcagt          20

<210> SEQ ID NO 42
<211> LENGTH: 21
<212> TYPE: DNA
<213> ORGANISM: murine

<400> SEQUENCE: 42
gtgatggagg cagacgattt g          21

<210> SEQ ID NO 43
<211> LENGTH: 20
<212> TYPE: DNA
<213> ORGANISM: murine

<400> SEQUENCE: 43
cctgaaacgt ccctgtgttt          20

<210> SEQ ID NO 44
<211> LENGTH: 20
<212> TYPE: DNA
<213> ORGANISM: murine

<400> SEQUENCE: 44
tgaacaggac agtgagccag          20

<210> SEQ ID NO 45
<211> LENGTH: 20
<212> TYPE: DNA
<213> ORGANISM: murine

<400> SEQUENCE: 45
gaacacggca aggtgaagat          20

<210> SEQ ID NO 46
<211> LENGTH: 20
<212> TYPE: DNA
<213> ORGANISM: murine

<400> SEQUENCE: 46
gagcgagaga caccaaggac          20

<210> SEQ ID NO 47
<211> LENGTH: 20
<212> TYPE: DNA

<213> ORGANISM: murine

<400> SEQUENCE: 47
aggctgtcct tggtcagaga                                               20

<210> SEQ ID NO 48
<211> LENGTH: 20
<212> TYPE: DNA
<213> ORGANISM: murine

<400> SEQUENCE: 48
tgtaactcca gttccagggg                                               20

<210> SEQ ID NO 49
<211> LENGTH: 20
<212> TYPE: DNA
<213> ORGANISM: murine

<400> SEQUENCE: 49
acgcccagct catgccaaca                                               20

<210> SEQ ID NO 50
<211> LENGTH: 20
<212> TYPE: DNA
<213> ORGANISM: murine

<400> SEQUENCE: 50
taaggccaca caattggcaa                                               20

<210> SEQ ID NO 51
<211> LENGTH: 20
<212> TYPE: DNA
<213> ORGANISM: murine

<400> SEQUENCE: 51
ggctgaagct ggtggtagag                                               20

<210> SEQ ID NO 52
<211> LENGTH: 20
<212> TYPE: DNA
<213> ORGANISM: murine

<400> SEQUENCE: 52
cccaggttgt caaagttgtc                                               20

<210> SEQ ID NO 53
<211> LENGTH: 20
<212> TYPE: DNA
<213> ORGANISM: murine

<400> SEQUENCE: 53
gcgagctggc tactatgacc                                               20

<210> SEQ ID NO 54
<211> LENGTH: 20
<212> TYPE: DNA
<213> ORGANISM: murine

<400> SEQUENCE: 54
cgttgctaat gctcacgaaa                                               20

<210> SEQ ID NO 55
<211> LENGTH: 20
<212> TYPE: DNA

<213> ORGANISM: murine

<400> SEQUENCE: 55
agatcaagca tctgcgtgtg 20

<210> SEQ ID NO 56
<211> LENGTH: 20
<212> TYPE: DNA
<213> ORGANISM: murine

<400> SEQUENCE: 56
tggaagctgg tctgtctcct 20

<210> SEQ ID NO 57
<211> LENGTH: 20
<212> TYPE: DNA
<213> ORGANISM: murine

<400> SEQUENCE: 57
gtgataacct cccagtgcgt 20

<210> SEQ ID NO 58
<211> LENGTH: 20
<212> TYPE: DNA
<213> ORGANISM: murine

<400> SEQUENCE: 58
aggatacaac agggcacgtc 20

<210> SEQ ID NO 59
<211> LENGTH: 20
<212> TYPE: DNA
<213> ORGANISM: murine

<400> SEQUENCE: 59
gagggaagca taggtcgtta 20

<210> SEQ ID NO 60
<211> LENGTH: 20
<212> TYPE: DNA
<213> ORGANISM: murine

<400> SEQUENCE: 60
tggaaggtgc caggttatgg 20

<210> SEQ ID NO 61
<211> LENGTH: 20
<212> TYPE: DNA
<213> ORGANISM: murine

<400> SEQUENCE: 61
accctggtgg atctcaagtg 20

<210> SEQ ID NO 62
<211> LENGTH: 20
<212> TYPE: DNA
<213> ORGANISM: murine

<400> SEQUENCE: 62
ggccacacag ggagtgtagt 20

<210> SEQ ID NO 63
<211> LENGTH: 20
<212> TYPE: DNA

<213> ORGANISM: murine

<400> SEQUENCE: 63
gatccaagaa gctggagcac                                          20

<210> SEQ ID NO 64
<211> LENGTH: 20
<212> TYPE: DNA
<213> ORGANISM: murine

<400> SEQUENCE: 64
ctcagtggtg cccctacaat                                          20

<210> SEQ ID NO 65
<211> LENGTH: 20
<212> TYPE: DNA
<213> ORGANISM: murine

<400> SEQUENCE: 65
cagcatgtct gacctctgga                                          20

<210> SEQ ID NO 66
<211> LENGTH: 20
<212> TYPE: DNA
<213> ORGANISM: murine

<400> SEQUENCE: 66
tatcttctgg cgcatgtcag                                          20

<210> SEQ ID NO 67
<211> LENGTH: 20
<212> TYPE: DNA
<213> ORGANISM: murine

<400> SEQUENCE: 67
ctgcgtgagg agattgtgaa                                          20

<210> SEQ ID NO 68
<211> LENGTH: 20
<212> TYPE: DNA
<213> ORGANISM: murine

<400> SEQUENCE: 68
gatctccccg aaataggagc                                          20

<210> SEQ ID NO 69
<211> LENGTH: 20
<212> TYPE: DNA
<213> ORGANISM: murine

<400> SEQUENCE: 69
cgtagctggg taccgtcaat                                          20

<210> SEQ ID NO 70
<211> LENGTH: 20
<212> TYPE: DNA
<213> ORGANISM: murine

<400> SEQUENCE: 70
acttggtgtg gacaaggagg                                          20

<210> SEQ ID NO 71
<211> LENGTH: 20
<212> TYPE: DNA

```
<213> ORGANISM: murine

<400> SEQUENCE: 71
cttctgctgt gtcactggga                                           20

<210> SEQ ID NO 72
<211> LENGTH: 20
<212> TYPE: DNA
<213> ORGANISM: murine

<400> SEQUENCE: 72
atactgcttc ccccaggagt                                           20
```

CARDIAC CONDUCTION SYSTEM CELLS AND USES THEREOF

CROSS-REFERENCE TO RELATED APPLICATIONS

This is a divisional of co-pending application Ser. No. 10/960,644, which claims the benefit of U.S. Provisional Application No. 60/578,676 filed Jun. 10, 2004.

FIELD OF THE INVENTION

The invention relates to the field of cardiology. The invention relates in particular to methods for modeling the cardiac conduction system and for the isolation and selection of cardiac conducting and pacing cells.

BACKGROUND OF THE INVENTION

The highly specialized cells of the cardiac pacemaking/conduction system (PCS) work together to initiate and synchronize atrial and ventricular contractions. The PCS includes proximal excitatory (nodal) cells and distal conducting, cells including ultimately the Purkinje cells. The excitatory nodal cells initiate excitation and directly cause the atrial cells to contract through rapid spread of depolarization through adjacent cells connected by gap junctions. The distal conducting cells convey the depolarization ultimately to the Purkinje cells, which cause the ventricular cells to contract. Dysfunction of this intricate electrical system results in cardiac arrhythmias or complete heart block and is a source of significant morbidity and mortality (Cheng C F, Kuo H C, Chien K R, *Trends Mol Med* 9 (2003) 59).

Localized in spatially discrete regions, the excitatory (nodal) cells are specialized non-contractile muscle cells that are able to produce intrinsic excitation in the absence of nervous innervation because they lack a stable resting membrane potential and are thus constantly depolarizing and drifting toward action potential in a spontaneous and rhythmic way. This is called autorhythmicity and these cells pace the heart and are thus termed "pacemaking" cells.

Pacemaking cells are spatially located primarily in the sinoatrial (SA) node, located in the right atrium where the superior vena cava enters the atrium, and secondarily in the atrioventricular (AV) node, located at the fibrous septum between the right atrium and the right ventricle. During a heartbeat, an action potential is generated in cells of the SA node, which have the fastest rate of depolarization. The action potential then spreads to two places, through gap junctions to the neighboring cells of atria, and to the internodal pathways. Internodal pathways are formed of specialized cells that act as a direct pathway for rapid conduction of the action potential to the AV node. These pathways do not use gap junctions to send impulses. The AV node, which has small diameter fibers and fewer gap junctions, delays and controls transmittal of the impulse to the AV or Common Bundle (Bundle of His), thus allowing time for the atria to finish contracting prior to ventricular contraction. The AV Bundle runs from the AV Node through the atrioventricular septum and then splits into the right and left bundle branches that run down the septum between the two ventricles and on through to the Purkinje fibers communicating the impulse to the ventricular muscle. As there are no electrical connections between cardiomyocytes of the atria and the ventricles, the AV Bundle is the only electrical connection between the atria and the ventricles.

Because adequate perfusion is vital to cellular life, cardiac development begins early in embryogenesis. Thus, the murine heart tube forms at approximately day 8 of embryonic development at which time slow, peristaltic contractions occur. This development can be recapitulated in vitro in embryonic stem cells that are allowed to begin differentiation. Embryonic stem (ES) cells are capable of differentiating into any cell type in the body including cells that constitute the specialized PCS in vivo. When murine ES cells are allowed to differentiate as clusters termed embryoid bodies (EBs), rhythmic spontaneous contractions can be observed between 8 to 10 days of differentiation, indicating the presence of cardiomyocytes. ES cells differentiated as EBs have been used to develop numerous model systems for studying cardiomyocyte differentiation because they closely recapitulate developmental gene expression patterns in vitro (Maltsev V A, et al., *Circ Res* 75 (1994) 233; M van Kempen et al., *Cell Physiol Biochem* 13 (2003) 263).

A primitive cardiac conduction system that recapitulates what is occurring during embryogenesis is also known to develop in embryonic bodies. The spontaneously contracting regions observed in differentiating EBs contain cells with electrophysiological characteristics of atrial, ventricular, and pacemaking/conducting myocytes (Wobus A M. et al. *Ann NY Acad Sci* 752 (1995) 460-9). Thus, in addition to the presence of contracting cardiac myocytes, specialized pacemaking and conducting cells are also present in developing liens and cells with "nodal-like" action potentials have been found in single-cell dispersions of EBs (Maltsev V A. et al., *Mech Dev* 44 (1993) 41). However, without performing electrophysiological experiments there has been no way to know which cells might be specialized pacemaking or conducting cells. While the development of electrical activity has been studied in EBs plated on multi-electrode arrays, this method provides only field potentials in the regions of the surface electrodes and is not always capable of identifying the specific cells that initiate or conduct the action potentials (Banach K, et al., *Am J Physiol Hear Circ Physiol* 284 (2003) H2114).

Based on the location of their expression in the heart, several genetic markers have been identified with components of the murine cardiac conduction system. However, it has been unclear whether cells expressing these markers actually function as specialized cardiac pacemaking or conducting myocytes (Myers D C & Fishman G I *Trends Cardiovasc Med* 13 (2003) 289-95; Tamaddon H S, et al., (*Circ Res* 87 (2000) 929-36; Rentschler S, et al., *Development* 128 (2001) 1785-92; Gourdie R G, et al., *Birth Defects Res Part C Embryo Today* 69 (2003) 46-57). Furthermore, because molecular markers of specialized cardiac conducting cells have not been heretofore undefined, it has remained unknown whether the spontaneously contracting regions are simply isolated groups of myocytes or groups of cells in a higher organization.

Several genetic markers have also been identified with components of the developing heart based through targeted disruption of genes and location of expression in the heart. Using a gene targeting knockout/knock-in approach, Kupershmidt S. et al., *Circ Res* 84 (1999) 146-52, reported that the endogenous expression pattern of minK, which encodes a β-subunit for the cardiac delayed rectifier potassium current ($I_K$), was localized to the central cardiac conduction system in mice and co-localized with connexin 40 in cells of the interventricular bundle branches. Expression of minK has been detected as early as embryonic day 8.25 in mice and continues to be expressed in adults, where it is confined primarily to the more proximal cardiac conduction system from the sinoatrial node through the interventricular bundles (Kondo R P, et al., *J Cardiovasc Electrophysiol* 14 (2003) 383). Although adult minK null mice are more prone to atrial arrhythmias than wild-type animals, they do not exhibit an overt altered phenotype.

Another marker that has been identified with discrete components of the specialized cardiac conduction system is the proximal 1.5 kb promoter/enhancer region of the chicken GATA6 gene (cGATA6) (Davis D L, et al. *Mech Dev* 108 (2001) 105-19). The zinc finger transcription factors GATA4-6 are expressed in the developing heart and participate in the activation of a variety of cardiac specific structural genes including α-myosin heavy chain (α-MHC), cardiac troponin-C, atrial natriuretic factor (ANF), brain natriuretic peptide and cardiac troponin-I. Expression of the GATA factors is transcriptionally regulated in a temporal and spatially specific manner through a network of interdependent regulatory events in which other factors interact with target regulatory regions in GATA promoter/enhancers. For example, in the mouse, the homeodomain protein Nkx2.5 binds to a defined region of the GATA6 enhancer and the ensuing regulatory circuit results in development of the cardiac crescent. (reviewed in Molkentin J D, et al., *Developmental Biology* 217 (2000) 301). Using lacZ expression as a reporter of cGATA6 enhancer activity in transgenic mice, Davis et al. (supra) demonstrated that cGATA6 is expressed in the cardiac primordia, (prior to expression of minK and the formation of the heart tube). Of all the reported markers of the cardiac conduction system, the cGATA6 enhancer exhibits the earliest and most restricted expression pattern (Wessels A, et al., *Novartis Found Symp* 250 (2003) 44-59; discussion 59-67, 276-9). In the adult mouse, expression becomes restricted to the proximal portion of the specialized cardiac conduction system.

It has emerged that the coordinate expression of discrete genes at specific stages of cardiac development is regulated through the choreographed action of particular sets of transcription factors acting in a sequence specific manner on various cardiac specific enhancers in the untranslated regions of both regulatory transcription factors and structural genes. However, because there are no model systems for studying the cardiac conduction system in vitro, little is known about the molecular identity of the cells that constitute the vital cardiac conduction system. Although several molecular markers have been shown to delineate components of the cardiac conduction system in vivo, the functional characteristics of the individual cells expressing these markers has remained unknown. (Myers D C and Fishman G I, *Trends Cardiovasc Med* 13 (2003) 289).

Assigning a molecular phenotype to cardiac myocytes from different regions of the heart is difficult. Currently, the most definitive way to characterize a cardiac myocyte is based on electrophysiological properties. Of the known cardiac-specific genes, there is no single gene that identifies a cardiac pacemaking or conducting cell. Most of the characteristics of pacemaking cardiac myocytes have been determined using freshly isolated cells. Both the SA and AV nodes are heterogeneous structures with regard to their cellular content. Part of the difficulty in identifying the cells that function as pacemaking cells in the heterogenous population is due to the lack of well-defined molecular markers.

Thus one of the biggest obstacles to isolating and studying cardiac pacemaking/conducting cells has been the absence of clear molecular markers for these cells that would enable isolation, enrichment and the development of model in vitro systems in which pacemaking cells can discriminated from conducting and contracting cardiomyocytes.

Genetic markers of the cardiac conduction system currently available have been designated as such based on the location of their expression. None of the putative markers of the cardiac conduction system have been shown to identify cells that actually function as specialized cardiac pacemaking or conducting cells and no one has isolated single cells expressing any of these markers to determine if these cells display characteristics of cardiac pacemaking or conducting cells.

What are needed are molecular markers for identification and isolation of the various component cells of the cardiac PCS both for the development of in vitro model systems and for isolation of cells for cardiotransplantation in the treatment of arrhythmia.

BRIEF SUMMARY OF THE INVENTION

The present invention provides markers for specialized cell of the cardiac pacemaking/conducting system (PCS). By identifying selected regulatory elements and harnessing these elements to direct the expression of marker genes, cells committed to both pacemaking and conducting phenotypes have been identified and isolated.

The invention provides nucleic acid sequences that regulate expression of nucleotide sequences in a manner that identifies cells of the cardiac pacing/conduction system. The invention also provides isolated pacemaking and conducting cells as well as methods of using these cells for the testing and derivation of pharmaceuticals in vitro and for repair of the PCS in vivo. In one embodiment, the invention described provides a method for the generation of an organized PCS.

In one embodiment, cGATA6 and minK markers are employed simultaneously in differentiating murine ES cells to provide a functional, organized cardiac pacemaking and conducting system in vitro.

In another embodiment of the invention, a cGATA6 enhancer identifies cells that organize and function as a pacemaking cells and is used to isolate a population of cells that resemble nodal cardiac myocytes with regard to gene expression and electrophysiological properties.

In one embodiment of the invention, a process is provided for the isolation and enrichment of specialized cells of the cardiac pacemaking system from stem cell populations including the steps of transfecting stem cells with an expression construct including a GATA6 regulatory element operably linked to a coding sequence for a surrogate marker, wherein the regulatory element is selectively active in cardiomyocytes that display or differentiate into the display of an $I_f$ pacemaking current. In one embodiment of the invention, the marker is selected from fluorescent proteins, enzymes, antibiotics, cell surface antigens, and combinations thereof. In one embodiment of the invention, the GATA6 regulatory element is derived from a chicken GATA6 promoter/enhancer.

In another embodiment, a method of identifying cardiac conducting system cells in a population of pluripotent cells is provided wherein expression is detected of a developmental stage specific protein selected from the group consisting of GATA6, minK, and combinations thereof. In one embodiment, expression of the developmental stage specific protein is detected by the expression of a surrogate for the developmental stage specific protein. In one embodiment, surrogate for the developmental stage specific protein is a marker expressed under the transcriptional control of regulatory elements that are derived from native promoter/enhancers for the developmental stage specific protein.

In one embodiment, a method of selecting pacemaking cells having the characteristics of sinoatrial node cells is provided including transfecting a stem cell with an expression construct encoding a selectable marker under the transcriptional control of regulatory elements derived from the GATA6 promoter/enhancer, selecting a population of cells expressing the selectable marker, and expanding the population of cells in vitro, thereby generating an enriched population of sinoatrial node cells. In one embodiment the stem cell is a mammalian embryonic stem cell and the selectable marker is selected from the group consisting of fluorescent proteins, enzymes, antibiotics, cell surface antigens, and combinations thereof.

In one embodiment, an organized cardiac pacemaking/conduction model system in vitro is provided including constituent single cells that display genetic and electrophysiological properties characteristic of specialized pacemaking/conducting cardiac myocytes.

In one embodiment, an organized cardiac pacemaking/conduction model system in vitro for determining the pharmacologic effects of compounds on cells of the mammalian cardiac conducting system is provided through the generation of a population of embryonic stem cells that have been selected for expression of a developmental stage specific protein selected from the group consisting of GATA6, minK, and combinations thereof. In one embodiment of the model system the cells are selected for expression of GATA6 and an $I_f$ current.

The process provides model systems that may be used for the in vitro testing of the activity of drugs on the cardiac conduction system. The invention further provides differentiated cell populations that may be used for developing novel therapeutic strategies for various forms of cardiac disease.

In a further embodiment the system employs co-expression of two molecular markers, GATA6 and/or minK, as reflected by the expression of surrogate markers.

In one embodiment of the present invention, molecular markers are provided that identify sub-populations of cells within differentiating EBs that organize in vitro to form a primitive, functional cardiac pacemaking, conduction, and contractile unit. In this embodiment of the invention, a system is provided in which cells active from the GATA6 and minK regulatory elements are co-selected and allowed to differentiate into subpopulations of cells in EBs that display characteristics of a working PCS including a nodal structure. Single cells expressing surrogate markers from both GATA6 and minK enhancer/promoters display action potential waveforms and hyperpolarization-activated cation currents ($I_f$) characteristic of specialized pacemaking cardiac myocytes. Adjacent to the GATA6/minK coexpressing cells, cells expressing minK alone organize into a transitional region that connects to contracting myocytes that are negative for expression from regulatory elements of the GATA6 and/or minK promoter/enhancers. The pacemaking and transitional cells function as a primitive pacemaking unit for control of contracting cardiac myocytes in EBs thus providing a unique system to study development and organization of the cardiac conducting system in vitro.

In one embodiment of the invention an in vitro model system is provided in which a 1.5 kb enhancer region of chicken GATA6 (cGATA6) and a 4.2 kb enhancer region of the murine minK gene, two putative markers of the cardiac conduction system, are used to define a pacemaking-conducting-contractile unit within differentiating embryonic stem (ES) cells. The model provides an in vitro model that closely resembles the anatomy of the mammalian PCS in that GATA6 expressing cells form a discrete cluster of pacemaking cells that are separated from contracting cells by minK only expressing cells that serve not only to transmit an action potential arising in the GATA6 pacemaking cells to the contracting cells but appear to also modulate this signal.

In another embodiment of the invention, the GATA6 enhancer is used to drive expression of a selectable marker, such as for example the neomycin resistance gene. When a population of neomycin-resistant cells is selected based on expression from GATA6 regulatory elements in differentiating EBs, the morphology of these cells resembles that of nodal (pacemaking) cells in animal hearts. Moreover, $I_f$ (pacemaking current) has been recorded in these cells.

The ability to isolate populations of pacemaking/conducting cardiac myocytes generates a model system for the testing and thus development of novel anti-arrhythmic drugs. Heretofore, there has been no way to develop drugs specifically for cardiac pacemaking/conducting myocytes because the molecular characteristics of these cells were not known. In addition to being used to generate cell-culture systems, this cell system permits the development of biological pacemakers or tissue-engineered cardiac structures to treat patients with heart disease.

DESCRIPTION THE DRAWINGS

FIG. 1: Graphical depiction of the relative differences in action potential in cells from different areas of the heart.

FIG. 2: General design of expression constructs according to one embodiment of the present invention. (A) minK; and (B) GATA6.

FIG. 3 A-F: (A) representative cGATA6-minK co-positive cell having a morphology corresponding with (C) a typical "nodal" spontaneous action potential. (B) another typical "atrial" cell like morphology observed in cGATA6-minK co-positive cells is shown with (D) a corresponding 4"atrial-like" action potential (stimulated) waveform. (E) Representative traces from a cGATA6-minK co-positive cell demonstrating the inward hyperpolarization-activated cation current characteristic of nodal cells. (F) Current-voltage relationship for hyperpolarization-activated currents measured in cGATA6-minK co-positive cells before (triangles) and after (squares) treatment with 10 mM cesium chloride. Points represent mean values at each membrane potential, error bars±standard error of the mean (SEM), n=16 cells.

FIG. 4: Processed image by overlapping phase contrast and fluorescent images using Metamorph software depicts a cardiac conduction system in embryoid bodies and shows co-expression of cGATA6 (red in color photograph, color not provided here) and minK (green in color photograph, color not depicted here) overlain on the corresponding phase-contrast image in a representative EB.

FIG. 5: Separating spontaneously contracting regions from cGATA6-positive cell clusters reduces spontaneous contraction frequency. (A) This representative region of an EB shows the spatial relationship between a cGATA6-positive cell cluster (red staining was found in the dense area on the right labeled "cGATA6") and an adjacent spontaneously contracting region on the left (labeled "contracting region"). (B) This is an image of the same region in FIG. 5(A) following physical separation of the cGATA6-positive cluster and the spontaneously contracting region. (C) Separating the cGATA6-positive cells from adjacent spontaneously contracting regions caused either a marked reduction or cessation of spontaneous contractions (* p<0.05, n=11).

FIG. 6: Sequence of the chicken GATA6 promoter/enhancer [−1.5/0.0] fragment.

FIG. 7 A-B: Sequence of a 4.2 kb murine minK enhancer region.

FIG. 8 A-F: (A) Shown are single cGATA6-neo cells 4 days following the end of G418 selection (day 16 of differentiation). (B) Approximately 10 days following G418 selection (day 22 of differentiation), cGATA6-neo cells are seen growing in clusters. (C) Representative traces from a cGATA6-neo cell demonstrating a voltage-gated calcium current (10 mV voltage steps from −80 to +60 mV from a holding potential of −80 mV) and (D) a graph of the average current-voltage relationship for the calcium current (n=6 cells). (E) Representative traces from a cGATA6-neo cell demonstrating the inward hyperpolarization-activated cation current and (F) a graph of the average current-voltage relationship (n=5 cells). Points represent mean values at each membrane potential, error bars±standard error of the mean (SEM).

DETAILED DESCRIPTION OF THE INVENTION

A primitive cardiac conduction system that recapitulates what is occurring during embryogenesis was known to develop in embryonic stem cells that are allowed to begin differentiation in embryonic bodies. In addition to providing models for studying cellular differentiation, ES cells give rise to functional cardiac myocytes exhibiting characteristics of atrial, ventricular, and nodal cells.

The presence of cardiac myocytes in developing EBs is classically confirmed by observing spontaneous contractions. Several groups have used micro-dissection to isolate spontaneously contracting regions and demonstrated the presence of cells resembling atrial, ventricular, and nodal myocytes based on their electrophysiological properties (Maltsev V A, et al. *Mech Dev* 44 (1993) 41-50; Zhang Y M, et al. *Am J Physiol Heart Circ Physiol* 285 (2003) H2770-9; Doevendans P A, et al. *J Mol Cell Cardiol* 32 (2000) 839-51). However, the organization of these cell types within intact EBs has never been fully appreciated due to a lack of appropriate molecular markers.

In addition, because molecular markers of specialized cardiac conducting cells were undefined, it remained unknown whether these contracting regions were simply isolated groups of myocytes or groups of cells in a higher organization. In order to identify, isolate, and expand specialized cardiac pacemaker/conducting cells, molecular markers had to be identified that could characterize the desired subpopulations of pacemaking and conducting cells.

By harnessing selected regulatory elements to direct the expression of surrogates, the present inventors have identified molecular markers of certain specialized cells of the PCS. In particular, the identification of these markers has been applied to the generation of cardiac pacemaker cells and cardiac conducting cells from embryonic stem cells.

Embryonic stem cells were first isolated from mice and were found to form aggregates or embryoid bodies in vitro that spontaneously differentiated into various cell types (Martin G. *Proc. Natl. Acad. Sci. USA* 78 (1981) 7634-7638; Evans M and Kaufman M. *Nature* 292 (1981) 154-156). Embryonic stem (ES) cells may be used as a source of cells that are capable of differentiating into many different cell types including cells potentially able to differentiate into cardiomyocytes. The term "embryonic stem cell" as used herein refers to a type of stem cell isolated from a morulae or the inner cell mass (ICM) of an in vitro fertilized embryo grown to the blastocyst stage. Fertilized eggs begin dividing and initially form a cluster of "totipotent" cells that are capable of developing into a complete organism or differentiating into any cell type of that organism. The cluster of totipotent cells begin differentiating to spherical body termed a blastocyst that has a discrete outer layer of cells and a morulae or inner cell mass (ICM) of cells. The ICM cells are "pluripotent" and thus cannot develop into a complete organism, but are able to differentiate into several different cell types.

ES cells are unique in their ability to grow relatively indefinitely in culture while retaining a normal karyotype. Murine ES cells can be cultured for many passages on gelatinized culture dishes in the presence of the cytokine Leukemia Inhibitory Factor (LIF), which causes them to remain in an undifferentiated state. (See Williams et al., U.S. Pat. No. 5,166,065). For differentiation, LIF is removed from the culture medium and cells are placed into suspension cultures in which they form aggregates called embryoid bodies (EBs).

The term "stem cell" generically refers to pluripotent cell. Stem cells are further defined by origin, such as for example, embryonic, adult, mesenchymal, etc. Although all stem cells can form cells of more than one different phenotype, and have the ability to proliferate including in in vitro culture through many divisions, the origin of the stem cell may limit the constellation of cell types that can form from it.

The term "embryoid bodies" refers to the aggregates of differentiated and undifferentiated cells of different cell types, typically from several germ layers that arise from the culture of ES cells under conditions that allow them to begin differentiation. Differentiating EBs theoretically contain every cell type found in the body and developmental gene expression patterns in EBs appear to mimic the patterns observed in vivo. However, because all of the normal developmental cues that dictate tissue organization are not present, the number and location of various types of cells within EBs has appeared to be somewhat random (Maltsev V A et al. (1994) *Circ Res* 75 (1994) 233-44; Hescheler J et al. *Cardiovasc Res* 36 (1997) 149-62).

One method of identifying genes important in lineage specific differentiation is to use molecular engineering to generate expression surrogates. Transcription control elements, herein termed "regulatory elements," that ordinarily control the expression of a particular gene are used to drive expression from marker or reporter genes in transgenic animal or transfected cells. The marker gene acts as a surrogate for detection of the genes and their respective control elements that are active in particular cells during unique spatial and temporal points in development.

Using such regulatory element driven marker expression, it was determined by He and Burch. *J Biol Chem* 271 (1997) 28550, that a 1.5 kb region immediately 5' to the chicken GATA6 coding sequence is required for expression of the atrioventricular canal of the developing heart. However, an additional of 7.7 kb was required for expression of the ventricle and outflow tract. Using lacZ expression as a reporter of cGATA6 activity in transgenic mice, it was demonstrated that cGATA6 is expressed prior to minK in the cardiac primordial prior to the formation of the heart tube, making it a very early marker. Expression of cGATA6 in the adult mouse becomes restricted to the proximal portion of the cardiac PCS including the atrioventricular (AV) node. (Davis D L et al., *Mech Dev* 108 (2001) 105-19. Based on the Kupershmidt report (*Circ Res* 84 (1999) 146-152), it was suggested in WO01/66814 that the minK promoter be tested for restricted or enhanced expression in the conduction system using a minK promoter-βGal reporter construct in transgenic mice.

The use of expression surrogates has also been used to isolate lineage committed cells as well as stem cells that can be maintained as undifferentiated pluripotent cells. In U.S. Pat. No. 5,639,618, Gay described a method for isolating lineage committed stem cells by transfection of a pluripotent embryonic stem cell with an expression construct having a regulatory region from a neurogenic lineage specific gene operably linked to a DNA encoding a reporter protein, culturing the cell under differentiation conditions, and then separating cells expressing the reporter.

The application of cardiac cell-specific promoter/enhancer elements to the selection of cardiomyocytes from embryonic stem cells has been reported, as well as the use of these selected cardiomyocytes in the formation of stable intracardiac grafts (Klug M G et al. *J Clin Invest* 98 (1996) 216-224 and U.S. Pat. No. 5,602,301 and related Reissue U.S. Pat. No. RE37,978, describing selection of cardiomyocytes from embryonic stem cells by co-transfection with a plasmid encoding antibiotic resistance under the control of the α-cardiac myosin heavy chain (α-MHC) promoter). In Lee and Izumo, WO01/51006, selection of cardiomyocytes after transfection with a plasmid encoding a selectable marker under the transcriptional control of Csx/Nkx2.5 was suggested based on cloning of murine Csx/Nkx2.5 promoter/enhancer elements. Likewise, Muller et al. *FASEB J.* 14 (2000) 2540-2548, described the isolation of a subpopulation of ventricular like cardiomyocytes by transfection with a vector having an expression construct encoding enhanced green fluorescent protein (EGFP) under the transcriptional control of the ventricular specific 2.1 kb myosin light chain-2v (MHC-2v) promoter coupled with the 0.5 kb CMV enhancer.

Conversely, the use of promoters active in very early development has been used to selecting for stem cells able to maintain an early lineage pluripotent phenotype from the differentiating cells of embryoid bodies. (i.e. U.S. Pat. No. 6,146,888 and U.S. patent application publication no. US 20020127715).

The use of expression surrogates for isolation of cells committed to a cardiac conduction system lineage by either positive or negative selection was suggested in WO01/68814. For negative selection, it was proposed that an embryonic stem cell or other multipotent cell could be provided carrying a negative selection gene such as the HSV thymidine kinase gene fused to a promoter which is inactive in conduction cardiomyocytes but active in other cardiomyocytes, for example the connexin 43 promoter, which is inactive in conduction cardiomyocytes. Differentiation of the stem cell was expected to result in mixed population containing conduction cardiomyocytes and other cardiomyocytes, e.g. working (contracting) cardiomyocytes.

Despite the identification of certain molecular markers for localization or selection of cell populations in the heart, including through the use of specific cardiac promoter/enhancer driven surrogate marker expression, molecular markers able to identify desired subpopulations of pacemaking and conducting cells has not been described and was needed in order to identify, isolate, and expand specialized cardiac pacemaker/conducting cells.

In order to provide genetic selection based on expression of cardiac-specific genes, the present inventors constructed numerous expression vectors containing different cardiac-specific regulators regions in order to determine those promoter/enhancer regions that are active in development of the PCS.

According to one embodiment of the invention. ES cells are transfected with vectors expressing marker genes under the transcriptional control of upstream regulatory elements (promoter/enhancer) that are active in cells of the developing cardiac conduction system during early embryogenesis. Markers such as for example, internally fluorescent proteins, detectable cell surface markers, and/or antibiotic resistance genes cells may be employed. The ES cells are then allowed to differentiate during the formation of EBs. Only cells that express the genes active in development of the cardiac conduction system will express the marker. Selected cells may be further selected on the basis of size by FACS. SA nodal cells have a characteristic small size.

In one embodiment, expression of two putative genetic markers of the cardiac conduction system GATA6 (portion of the GATA6 promoter/enhancer proximal to the transcript start) and minK were used to study the development of a discrete sub-population of cells in differentiating EBs. It was known that in developing embryos, expression of GATA6 or minK is confined to regions of the heart corresponding to the location of the specialized conduction system, particularly the proximal (SA node to the interventricular bundles) cardiac conduction system.

The term minK (a.k.a. Kenel, IsK-related subfamily, member 1) protein is used herein to describes a small protein (129 amino acids in mouse and human) representing the $I_{Ks}$ β-subunit and that functions to modulate the cardiac delayed rectifier potassium currents ($I_K$) resulting from expression of HERG and KvLQT1, which encode the structural α-subunits for the channels underlying the cardiac delayed rectifier currents $I_{kr}$ and $I_{ks}$ respectively and is thus important to cardiac repolarization. The distribution of minK corresponds with the conduction system and cells expressing minK co-stain with connexin 40. Connexin 40 (CX 40) is expressed specifically in cells of the mouse conducting system but not in working myocytes. Conversely, connexin 43 is expressed primarily by working ventricular and atrial cardiomyocytes. The connexins are the component proteins of gap junction channels. Gap-junctional channels composed of different connexin types exhibit different biophysical properties, including distinct conductance, ionic selectivity and molecular permeability properties. Thus, spatially defined expression patterns of connexins 43, 40 and 45 participate in forming the architecture of the cell-to-cell conduction pathways that permit the orderly spread of current flow resulting in normal cardiac rhythm.

The expression of lacZ in the minK-lacZ knock-in mice is known to be restricted to discrete regions of the right atrium, extending down through the AV node and interventricular bundles (Kupershmidt S et al. *Circ Res* 84 (1999) 146-52; Kondo R P et al. *J Cardiovasc Electrophysiol* 14 (2003) 383-91). The cGATA6 enhancer also marks the AV node and discrete regions in the right atrium including the SA node (Davis D L et al. *Mech Dev* 108 (2001) 105-19; Edwards A V et al. *Novartis Found Symp* 250 (2003) 177-89; discussion 189-93, 276-9). Because the expression patterns from minK-lacZ and the cGATA6 enhancer are similar in vivo, the present inventors examined the expression of both markers simultaneously to determine if they identify the same cells. EBs generated from ES cells containing the minK-lacZ targeting vector were fixed and stained them for β-galactosidase expression. In all EBs stained, discrete clusters of cells developed that express β-galactosidase and, hence, the minK-lacZ transgene.

The term "GATA6" is used to describe a transcription factor that is active in early cardiac development. GATA6 is a member of the GATA family of zinc finger transcription factors (GATA 1-6). (Laverriere A C et al., *J Biol Chem* 269 (1994) 23177-23184). The proximal 1.5 kb promoter/enhancer region of the chicken GATA6 gene (cGATA6) has been used to identify more discrete components of the specialized cardiac conduction system (D L Davis et al. *Mech Dev* 108 (2001) 105). Using lacZ expression as a reporter of cGATA6 activity in transgenic mice, it was demonstrated by Davis et al. that GATA6 is expressed prior to minK in the cardiac primordial prior to the formation of the heart tube, making it a very early marker.

However, prior to the present invention, only the characteristics of the respective times of expression of GATA6 and minK in tissue development had been described, but not the characteristics of individual expressing cells. In order to ensure that GATA6 and minK are expressed in differentiating EBs, the present inventors introduced vectors into ES cells such that expression of reporter genes is controlled by regulatory regions derived from either the GATA6 or minK genes. In accordance with one embodiment, after the transfected cells are allowed to differentiate into EBs, cells that are transcriptionally active from either the GATA6 or minK regulatory elements will express the marker gene and are identified, isolated and characterized.

If for example, lacZ is used as the marker, cells transcriptionally active from regulatory regions derived from either the GATA6 or minK genes will appear blue upon exposure to the substrate for the lacZ enzyme. Using lacZ as the marker, development of discrete evolving populations was demonstrated after fixing and staining of EBs containing cells expressing each of the two cardiac conduction system markers, GATA6 and mink.

Thus, in one embodiment of the invention, undifferentiated murine J1ES cells were transfected with expression vectors to create the 3 genetically-modified populations of cells containing the vectors cGATA6→RFP, minK→lacZ, and cGATA6→RFP+minK→lacZ. The minK-lacZ targeting vector was transfected into a separate population of ES cells as well as the same ES cells containing the cGATA6→RFP vector allowing the study of the two putative markers of the cardiac conduction system separately and simultaneously. These genetically-altered ES cells were differentiated as embryoid bodies (EBs) using the hanging-drop method. Spontaneously contracting regions were detected in approximately 75% of EBs at day 8 of differentiation in all groups (cGATA6, mink, and cGATA6/minK).

In order to demonstrate the functional attributes of cells active from either the GATA6 or mink regulatory elements in living cells, vectors were utilized in which expression of different fluorescent markers was controlled by either the GATA6 enhancer (Red Fluorescent Protein or RFP) or the minK enhancer (lacZ expression monitored using a vital, fluorescent substrate, fluorescein di-galactoside from Molecular Probes, which fluoresces green and allows detection without fixing the cells). These expression vectors were then introduced into undifferentiated ES cells to create a stable, genetically altered cell line. This ES cell line has provided an extremely powerful tool for studying the expression of two molecular markers simultaneously during differentiation. Additionally these markers allowed the identification and separation of these cells from all other cell types found in the EBs.

Imaging EBs for GATA6-positive and minK-positive cells revealed an organization resembling the pacemaking-conducting-contractile organization found in the heart. In the heart, myocytes of the pacing/conducting system (PCS) include the excitory sinoatrial (SA) node and atrioventricular (AV) node cells (pacemaking cells) as well as conducting cells. Sinoatrial node cells can be identified from surrounding atria cells by a number of physical characteristics. Physical characteristics of the typical cells of the central SA node are a characteristic staining pattern, a smaller size than surrounding atrial cells and the presence of few poorly organized myofilaments. Cells in the center of the SA node cells are termed "P" or "pale" cells. As a consequence of the fewer myofibrils of nodal cells, they appear pale in light microscopy. Cells having this morphology are considered "typical nodal" cells. (MR Boyett et al. *Cardiovascular Res* 47 (2000) 659-687).

SA node cells display a characteristic delayed rectifier $K^+$ current ($I_K$) and hyperpolarization-activated ($I_f$) currents that reflect the fastest rate of diastolic depolarization among cardiomyocytes. Hyperpolarization-activated ($I_f$) currents are also termed "funny" currents. In the heart, the pacemaking and specialized conducting cells do not contain the sarcomeric organization exhibited by atrial and ventricular myocytes since they do not serve a contractile function.

As used herein, the terms "pacing cell" or "pacemaking cell" are used interchangeability to refer to cells having the physical characteristics of the typical nodal cells of the central SA node including the above described characteristic staining pattern, a smaller size than surrounding atrial cells, the presence of few poorly organized myofilaments and displaying the characteristic hyperpolarization-activated ($I_f$) currents. As used herein, the phrase "pacemaking/conducting cells", abbreviated PCS, refers to non-contracting cardiomyocytes of the cardiac conduction system. The pacemaking cells include SA and AV node cells. The conducting cells include internodal cells, and cells of the Bundle of His and right and left bundles, as well as Purkinje cells.

The present inventors surprisingly found that GATA6- and minK-positive cells co-localize adjacent to spontaneously contracting regions in the EBs. In fact, cGATA6-positive cells appear to represent a sub-population of minK-positive cells, which extend and merge into contracting regions. Although their expression patterns in vivo seem to partially overlap, the present inventors determined that the cGATA6 enhancer identifies more discrete populations of cells. In EBs, cGATA6-positive cell clusters could be identified at day 5 of differentiation while minK-positive cells were observed at day 8, which is when spontaneous contractions are first observed in the EBs. cGATA6 cells are mostly present in fairly compact clusters, while cells expressing the minK-lacZ transgene are more diffuse. Approximately 80-90% of cGATA6-positive cells are also minK-positive, and they seem to represent a sub-population of the minK-positive cells.

The present inventors found GATA6-positive ells, considered to represent a small "nodal" phenotype, located near, but not in mechanically contracting regions of EBs. In EBs, every spontaneously contracting region observed was associated with a cGATA6- and minK-positive cell cluster. Approximately 10% of the EBs observed did not contain cGATA6- and minK-positive cell clusters. These same EBs also contained no spontaneously contracting regions.

The cGATA6-positive cells were always separated from the spontaneously contracting regions by a "bridging" minK-positive region, which is similar to nodal organization in vivo with the presence of transitional myocytes. (Additionally, in vivo the AV node is functionally coupled with the contracting ventricular myocardium by the rapidly conducting interventricular bundle branches. (Anderson R H & Ho S Y. *J Cardiovasc Electrophysiol* 9 (1998) 1233-48). The transitional cells are minK positive but GATA6 negative. GATA6-positive cells represent a subpopulation of the minK-positive cells organized in clusters throughout EBs. When examining spontaneously contracting regions of EBs, it appears as though the GATA6-positive clusters act as pacing "nodes" for nearby contracting regions.

The functionality of the in vivo cardiac conducting model was tested. Nodal cardiac myocytes spontaneously depolarize to generate electrical impulses that are propagated to "working" myocytes causing contractions. These spontaneous depolarizations are caused primarily by calcium influx.

To further determine that GATA6-positive cells function as pacemaking cells in EBs, EBs were loaded with a calcium-sensitive dye that fluoresces in the presence of free intracellular calcium. Increases in intracellular calcium were detected and localized in EBs containing GATA6-positive cells indicating a higher basal intracellular calcium concentration compared to surrounding cells. In cardiac myocytes, the intracellular calcium concentration increases in response to a depolarizing stimulus. Therefore, in cardiac myocytes, calcium transients are directly proportional to cellular depolarization.

When EBs were incubated with a calcium-sensitive dye to image calcium fluxes, rhythmic, spontaneous calcium oscillations were detected being emitted from cGATA6-positive cell clusters into the surrounding contracting regions. Using EBs loaded with a fluorescent, calcium-sensitive dye, spontaneous calcium transients could be detected in cGATA6-positive cell clusters at day 6 of differentiation, prior to the onset of spontaneous contractions, and continued after the onset of spontaneous contractions. This indicates that nodal myocytes develop functional pacemaking properties prior to the onset of visible contractions.

Following the onset of spontaneous contractions (day 8), calcium sparks could be seen emitting from cGATA6-positive cells into nearby contracting regions. Interestingly, calcium transients seem to emerge from the GATA6-positive cells and then spread to surrounding cells, including contractile cardiac myocytes. This data provides evidence that the GATA6-positive cells serve as pacemaking cells for neighboring contracting cardiac myocytes in EBs.

The ultimate test for the presence of functional pacemaking cells is to uncouple the pacemaking cells from the contracting cells and observe a change in contraction rate. Thus, in order to test whether these cells do, in fact, function in EBs as pacemakers, a scalpel was attached to a micromanipulator to physically separate GATA6-positive cellular clusters from associated spontaneously contracting regions of EBs (FIG. 5B). In 3 of the EBs, spontaneous contractions ceased, while in 6 EBs, the contraction rate decreased from an average of 75 contractions/min. to 40 contractions/min. This response mimics nodal dysfunction in the intact heart. In a further test, when cGATA6-positive cell clusters were physically separated from adjacent contracting regions, contraction rates decreased from 52±11/min. to 12±10/min. (n=11 EBs) before and after separation. (FIG. 5 (C). By demonstrating that the rate of spontaneous contractions in EBs is dependent on physical coupling with cell clusters marked by the cGATA6 enhancer, these cells were shown to function as pacemaking cells in a multicellular environment.

Having determined that cells identified by the cGATA6 enhancer and the minK-lacZ transgene function as specialized pacemaking/conducting cells in vitro, single cells from the EBs were isolated to determine their electrophysiological properties. Because each cardiac-specific cell population has a distinct action potential waveform (FIG. 1), determining the action potential may be used to functionally characterize a cardiomyocyte population. Based on action potential waveforms, cells can generally be classified as nodal (SA or AV), atrial, distal conducting (His~Purkinje), or ventricular. The differences in the action potential waveform shapes from various cardiac myocytes are due to the relative levels of expression of specific ionic currents. One common characteristic of cells of the specialized cardiac pacemaking and conducting system is the relatively high expression of the hyperpolarization-activated (funny) pacemaking current ($I_f$), considered to be one of the primary currents involved in cardiac pacemaking.

Electrical currents can be assessed in single cells using a technique called patch-clamping. Using this technique, a micropipette containing an electrode is introduced into single cells to measure the action potential and identify the cell type generally in accordance with the patterns depicted in FIG. 1.

Thus, in addition to defining the GATA6-positive cells in the context of intact, differentiating EBs, the patch-clamp technique was used to study electrophysiological characteristics of these single cells. On the day prior to experiments, EBs are disrupted using trypsin and mechanical dissociation to yield single cells and plated onto coverslips. For patch-clamp studies, coverslips are placed into a recording chamber on an inverted Nikon microscope. A whole-cell configuration of the patch-clamp technique in current-clamp mode is used to show that these cells display action potentials characteristic of cardiac myocytes.

Using the whole-cell configuration of the patch-clamp technique, it was determined by the present inventors that, although cGATA6/minK co-positive cells are heterogeneous with respect to their action potential waveforms (exhibit both nodal and atrial), all of these cells express a significant, cesium-sensitive $I_f$.

The hyperpolarization-activated ("funny") pacemaking current ($I_f$) was detected in cGATA6 and minK positive cells at average densities of 25±10 pA/pF and 20±15 pA/pF, indicating that these two molecular markers identify sub-populations of cells with characteristics of specialized conducting cardiac myocytes. Thus a model system is provided in which cGATA6 and minK positive cells function in regulating spontaneous contractions in differentiating EBs and express the $I_f$ pacemaking current. In studying these single cells, it was determined that almost all of the GATA6-positive cells also express mink, but the reverse is not true.

Although the electrophysiological properties of cardiac pacemaking cells are fairly well established, the molecular phenotype of these cells has remained mystery. In order the characterize the molecular phenotype of the GATA6-positive pacemaking cells, a population of cells was selected that express the neomycin resistance gene under control of the cGATA6 enhancer to analyze the expression of a panel of cardiac genes encoding transcription factors, structural and sarcomeric proteins, ion channels, and gap junction proteins. Some of the results provided novel insight into the regulation of these unique cells. The cGATA6-neo cells express significant levels of nkx2.5, GATA4, GATA6, α- and β-mhc, and desmin, which confirm their identity as cardiac myocytes. See Sachinidis A et al. *Cardiovasc Res* 58 (2003) 278; Doevendans P A & van Bilsen M. *Int J Biochem Cell Biol* 28 (1996) 387. The cells also express a high level of mlc-2a (an atrial-specific myosin light chain isoform) and no detectable mlc-2v (a ventricular-specific isoform). Because the SA and AV nodes are located in the right atrium, the mlc-2a expression supports their nodal phenotype.

Of 9 transcription factors analyzed, the two most highly expressed are msx2 and GATA6. Nodal cells are considered to represent primitive cardiac myocytes that have not initiated a "chamber-specific" gene expression pattern (Moorman A F & Chliistoffels V M. *Novartis Found Symp* 250 (2003) 25-34, discussion 34-43, 276-9). Most of the information regarding the function of msx2 is in the context of limb development and tissue regeneration (Carlson M R et al. *J Exp Zool* 282 (1998) 715; Nechiporuk A & Keating M T. *Development* 129 (2002) 2607). In the heart, msx2 expression has been found only in portions of the specialized conduction system (Chan-Thomas P S et al. *Dev Dyn* 197 (1993) 203-16). The fact that msx2 is expressed at an extremely high level in the cGATA6-neo cells supports the idea that these are primitive (less differentiated) cells. In *Xenopus*, increased expression of gata6 delays myocardial differentiation (Brewer A et al. *J Biol Chem* 274 (1999) 38004).

Another transcription factor expressed at a high level in the cGATA6-neo cells is tbx3. Moorman and Christoffels have shown that tbx2 and tbx3 bind nkx2.5 and repress the transcription of "chamber-specific" genes such as anf and connexin 40, thereby marking primitive cardiac myocytes (Moorman A F & Christoffels V M. *Novartis Found Symp* 250 (2003) Supra). Both anf and connexin 40 are expressed at very low levels in cGATA6-neo cells. Recently, it was shown that tbx3 becomes restricted to the SA and AV nodes and an internodal tract in adult mice (Hoogaars W M, et al. *Cardiovasc Res* 62 (2004) 489-99).

Thus, in one embodiment, the present inventors have developed and characterized a model in which co-expression of the two molecular markers cGATA6 and minK in differentiating ES cells reveal a functional cardiac conduction system in vitro. cGATA6-positive cell clusters act as pacemaking units that functionally couple with nearby contracting regions of EBs. This EB model system and the pacemaking/conducting cells identified by these markers provide an invaluable tool for studying the fundamental biology of cardiac pacemaking cells, designing targeted pharmaceutical agents, and developing novel cellular and tissue-engineered therapies. By isolating ES cell-derived cardiac myocytes with a nodal phenotype, a cell model system has been generated that can be used to probe the differentiation and molecular regulation of cardiac pacemaking cells.

The present inventors have also surprisingly found that cells selected on the basis of cGATA6 activation can be stably maintained in a relatively primitive nodal cell state of differentiation through serial passage or, alternatively, can be induced into different phenotypes through manipulation of culture conditions. Thus, in another embodiment, after surrogate marker selection based solely on transcriptional activity relating to a GATA6 enhancer, cells can be maintained in a nodal phenotype through serial passage and used as a source for nodal cell studies, drug testing for effects on nodal cell function or transplantation to supplement pacemaker cell insufficiencies. However, if desired, these cells can alternatively be converted to more terminally differentiated contractile cells by altering culture conditions. In one embodiment, stable cell populations derived originally by surrogate marker selection based on the cGATA6 promoter/enhancer are induced to differentiate into contractile atrial type cells by culturing in differentiation media. In one embodiment, the differentiation media contains supplements selected from the group: norepinephrine, insulin, ascorbic acid and combinations thereof. Such cells are then useful for contractile cell studies, drug testing for effects on contractile cell function or transplantation to repair damage to the myocardium.

As used herein, the phrase "promoter element" means nucleic acid sequences that are able to engage and drive the transcription apparatus resulting in the production of a transcript. The phrase "enhancer element" means a nucleic acid sequence that is able to augment expression from a promoter. Enhancer elements are typically located in proximity to promoter elements and are upstream of a coding sequence. However, an enhancer element can be located within introns or downstream of the coding sequence. As the boundary between promoter and enhancer elements may be difficult to define where both elements are located upstream of a coding sequence, the combined term promoter/enhancer is often used or the term promoter may be used to encompass both promoter and enhancer.

The phrase "GATA6 regulatory element" as used herein means nucleic acid sequences that are derived from a GATA6 promoter, enhancer or promoter/enhancer and naturally participate in the controlled spatial and temporal expression of the GATA6 transcription factor. When used in conjunction with surrogate makers, GATA6 regulatory elements permit a discernable reflection of the expression of GATA6. One example of a nucleotide sequence that contains a GATA6 regulatory element is the −1.5 to −0.0 kb proximal region of the chicken GATA6 promoter/enhancer. Using the present system as a benchmark or "control" for the desired in vitro differentiation phenotype, further regulatory elements may be isolated by molecular engineering including subset sequences, synthetic sequences and chimeric sequence, including those derived from the GATA6 promoter/enhancer of other species including from human, mouse, etc. GATA6 regulatory elements may be combined with additional promoter and enhancer elements as long as they continue to reflect controlled spatial and temporal expression of the GATA6 transcription factor.

The phrase "minK regulatory element" as used herein means nucleic acid sequences that are derived from a minK promoter, enhancer or promoter/enhancer and naturally participate in the controlled spatial and temporal expression of the minK structural protein. When used in conjunction with surrogate makers, minK regulatory elements permit a discernable reflection of the expression of minK. One example of a nucleotide sequence that contains a minK regulatory element is the −4.0 to +0.2 kb region of the minK genomic sequence proximal to the initiator codon of the murine minK coding sequence. This region is primarily intronic. Using the present system as a benchmark or "control" for the desired in vitro differentiation phenotype, further regulatory elements may be isolated by molecular engineering including subset sequences, synthetic sequences and chimeric sequence, including those derived from the minK promoter and/or enhancers of other species including human, etc. MinK regulatory elements may be combined with additional promoter and enhancer elements as long as they continue to reflect controlled spatial and temporal expression of the minK structural protein.

The term "regulatory element" as used herein means any nucleotide sequence that increases or decreases transcriptional expression from a coding sequence to which it is operably linked. The regulatory element may be sufficient for transcription and thus be considered to be the promoter, or may work in concert with a promoter and be an enhancer element. Alternatively the regulatory element may be a promoter-enhancer combination. By molecular engineering, these regulatory elements can be exploited to drive the expression of marker genes, which are then expressed in the same temporal and spatial fashion as the coding sequences with which the expression regulatory sequences are naturally apart.

The phrase "regulatory element driven selection" as used herein refers to the use of expression regulatory sequences to drive expression of marker genes under such temporal and spatial conditions as the expression regulatory sequences would ordinarily drive expression of the genes to which they are naturally apart. The marker gene acts as a "surrogate" for expression of the gene to which the regulatory element is normally a part. As used herein, the phrase "regulatory element driven selection" is synonymous with "surrogate marker selection." The marker can be any detectable expressed gene product including, for example and without limitation, fluorescent proteins, enzymes, antibiotics, cell surface antigens, and combinations thereof.

The regulatory element referred to above may be a regulatory sequence for a "developmental stage specific protein", which is defined as a structural or regulatory protein that has been observed to be expressed in a discrete temporal and/or spatial pattern during development. GATA6 and minK are developmental stage specific proteins under this definition.

The terms "vector" or "expression vector" as used herein refer to a replicatable nucleic acid expression system, such as an autonomous self-replicating circular DNA (e.g., a plasmid) or virus, which is able to transfer an "expression construct" from one host to another. Typically, the vector does not replicate in the final host in which expression takes place.

By "expression construct" is meant a nucleic acid molecule that includes a transcribable sequence including a coding sequence for a product of interest. The expression construct enables expression of the product at an elevated level and has been designed as a functioning genetic unit capable of directing transcription of the coding sequence into a functional RNA. The product of interest encoded by the coding sequence may be a polypeptide or a RNA such as an antisense-RNA. An expression construct of the present invention includes, at the least, a regulatory element and a coding sequence. The terms "polypeptide", "peptide" and "protein" are used interchangeably in this disclosure to refer to polymers of amino acids of any length.

The phrase "operably linked" as used herein refers a physical and functional relationship. Thus, promoters operably linked to a coding sequence are able to effect expression of the coding sequence. Genetic elements are said to be "operatively linked" if they are in a structural relationship permitting them to operate in a manner according to their expected function. For instance, if a regulatory element such as a promoter helps initiate transcription of the coding sequence, the coding sequence can be referred to as operatively linked to (or under control of) the promoter. There may be intervening sequence between the promoter and coding region so long as this functional relationship is maintained.

The terms "transfected" and "transfection" as used herein refer to methods of delivering exogenous DNA into a cell or cells in a population. Transfection may occur in vivo as well as in vitro. For purposes of the present invention, a transfected cell and its progeny can be said to be "genetically altered", "transfected", or "transformed" by the nucleic acid where the introduced nucleic acid results in a measurable change in the cell, typically manifest as a phenotypic change. Transfection may be accomplished by a variety of techniques, including without limitation, physical methods such as electroporation and sonoporation, or may be facilitated by chemical methods including through the use of liposomes, cationic lipids and other cationic compounds that physically associate with the DNA, ionic and non-ionic compounds and detergents, etc. that increase the ability of the exogenous DNA to enter host cells. These specified methods are not limiting and may be accomplished by any relevant technique well known to a person of ordinary skill in the art.

General techniques useful in the practice of this invention are known to those of skill in the art as detailed in standard textbooks, handbooks and reviews in cell biology, tissue culture, molecular genetics, genetic engineering, embryology and cardiology. Included are *Molecular Cloning: A Laboratory Manual*, (Sambrook et al.); *Oligonucleotide Synthesis* (Gait M J, ed.,); *Animal Cell Culture* (3$^{rd}$ Ed., edited by John R W Masters); and *Current Protocols in Molecular Biology and Short Protocols in Molecular Biology*, 3rd Edition (Ausubel F M et al., eds.). Reagents, cloning vectors, and kits for genetic manipulation referred to in this disclosure are available from commercial vendors such as Sigma, Invitrogen, Stratgene and ClonTech, among others.

The following examples illustrate certain aspects of the above-described method and advantageous results. The following examples are shown by way of illustration and not by way of limitation.

Example 1

System Development and Characterization

The expression of lacZ in the minK-lacZ knock-in mice is restricted to discrete regions of the right atrium, extending down through the AV node and interventricular bundles (Kupershmidt S et al. *Circ Res* 84 (1999) 146; Kondo R P et al. *J Cardiovasc Electrophysiol* 14 (2003) 383). The cGATA6 enhancer also marks the AV node and discrete regions in the right atrium including the SA node (Davis D L et al. *Mech Dev* 108 (2001) 105; Edwards A V et al. *Novartis Found Symp* 250 (2003) 177-89; discussion 189-93, 276-9). Based on an appreciation that expression patterns of minK-lacZ and the cGATA6 enhancer are similar in vivo, the present inventors undertook an examination of expression of both markers simultaneously to determine if they identify the same cells. In order to get an idea of the expression pattern of these markers, EBs generated from ES cells containing the minK-lacZ targeting vector were fixed stained them for β-galactosidase expression. In all of the EBs stained, discrete clusters of cells expressing β-galactosidase and, hence, the minK-lacZ transgene were observed.

Culture of ES cells: Murine J1 embryonic stem "ES" cells (provided by Rudolf Jaenisch, and as described in Li E. Bestor T H, Jaenisch R. *Cell* 69 (1992) 915) were cultured as follows: Dulbecco's modified Eagle medium (DMEM) (Invitrogen) supplemented with 0.1 mM non-essential amino acids (NEAA) (Invitrogen), 100 U/mL: 100 μg/mL penicillin: streptomycin (Invitrogen), $10^{-4}$ M β-mercaptoethanol, and 10% fetal bovine serum (FBS) was used as the base medium for culturing both undifferentiated and differentiating ES cells. The ES cells are maintained in an undifferentiated state by culture with the base medium described above supplemented with 1000 U/mL leukemia inhibitory factor (LIF) (Chemicon). Human and murine recombinant LIF are disclosed in Gearing at al., U.S. Pat. No. 5,187,077. Undifferentiated ES cells are passaged using 0.05% trypsin-EDTA every 48 hours and plated onto 10 cm$^2$ 0.1% gelatin-coated culture dishes with a split ratio of approximately 1:6.

Differentiation of ES cells: In development of the present invention, efforts were undertaken to develop and confirm methods for isolating stem cells able to differentiate into cells of the pacing/conducting system. It was known that as embryoid bodies ("EBs") differentiate, spontaneously contracting regions can be observed and that these spontaneously contracting regions contain cells with electrophysiological characteristics of atrial, ventricular, and pacemaking/conducting myocytes (Wobus A M et al. *Ann NY Acad Sci* 752 (1995) 460). Techniques relating to ES and EB cell culture and manipulation are generally outlined in Maltsev V A et al. *Mech Dev* 44 (1993) 41.

Briefly, 20 μL drops containing 200 ES cells each in differentiation medium (growth medium without leukemia inhibitory factor) were placed on non-treated tissue culture Petri dishes (Fisher), which were inverted for 2 days. These EBs in hanging drops were then suspended in differentiation medium in the same dishes for an additional 5 days. At day 7 of differentiation, EBs were plated onto tissue culture dishes coated with 0.1% gelatin where they remained until used for experiments.

Figure 2A:
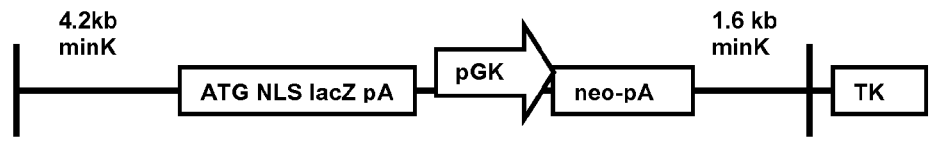

Generation of a model conduction/pacing system: Undifferentiated ES cells were transfected with linearized minK-lacZ targeting vector. A minK-lacZ targeting vector was provided by Dan Roden and Sabina Kupershmidt, as described in S Kupershmidt et al. *Circ Res* 84 (1999) 146). The construct as generally depicted in FIG. 2A includes approximately 4.2 kb of genomic sequence immediately 5' to the initiator ATG of the minK coding sequence, as well as 1.6 kb of genomic sequence immediately 3' to the minK coding sequence. A genomic sequence for the 4.2 kb of 5' upstream sequence to the murine minK coding region, SEQ ID NO:2, is reproduced on FIG. 7. Essentially all of the minK enhancer sequence employed is from the 2nd intron of the initial transcript. In the targeting vector used, the minK coding sequence was replaced with a lacZ coding sequence followed immediately by a phosphoglycerate kinase promoter driving expression of neo$^r$. Thus, expression of lacZ is influenced by the minK regulatory element. The minK-lacZ vector was linearized for transfection of undifferentiated ES cells using the cationic lipid transfecting agent LF2000 (Invitrogen) according to the manufacturer's protocol. Transfected ES cells were cultured for 7 days in the presence 300 μg/mL G418 (AG Scientific) and 20 μM ganciclovir (Sigma).

Figure 2B:
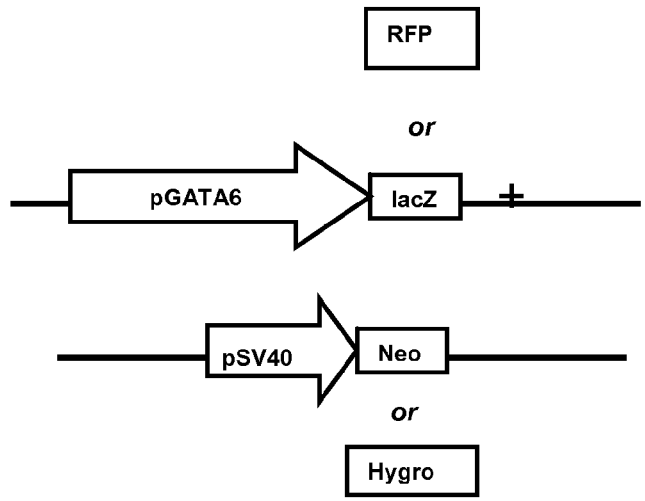

Following a second period of selection in the same concentrations of G418 and ganciclovir, the undifferentiated ES cells containing the minK-lacZ expression vector were co-transfected with the linear chicken GATA6-1.5/0.0 kb enhancer (cGATA6)-ERFP vector and a linear pcDNA3.1(+)-hygro vector (Invitrogen) using LF2000 and selected with 300 μg/mL hygromycin (Sigma) for 7 days. A general map of the GATA6 expression vector construct is depicted in FIG. 2B (pGATA6). The proximal 1.5 kb (−1.5/0.0) region of the chicken GATA6 promoter/enhancer (cGATA6) (provided by John Burch, as described in D L Davis et al. *Mech Dev* 108 (2001) 105) was inserted into the SalI and BamHI sites in the multiple cloning site of a promoter-less enhanced red fluorescent protein (ERFP) vector (Clontech). Thus, expression of ERFP is controlled by the cGATA6 regulatory element. In FIG. 6 the sequence of the cGATA6 promoter is provided (SEQ ID NO: 1) with the regions of the cGATA6 promoter that are identical to the mouse and human GATA6 promoters highlighted and underlined.

Once undifferentiated ES cells containing vector constructs (for example, minK-lacZ or minK-lacZ and cGATA6-ERFP) were generated, they were differentiated using the hanging drop method as previously described. Some EBs were fixed and stained for β-galactosidase expression using the Stratagene β-galactosidase Staining Kit. Imaging (fluorescent and phase/contrast) was performed using a Nikon microscope along with Metamorph Software (version 5.0 v6, Advanced Scientific). For visualizing minK-positive live cells, EBs were incubated the day of recording for 20 min. at 37° C. in medium containing the fluorescent β-galactosidase substrate fluorescein di-galactoside (20 μM FDG-C12) (Molecular Probes). Cells were then washed with PBS and incubated for 1 hour in differentiation medium prior to visualization.

In EBs generated from ES cells expressing both minK-lacZ and cGATA6-enhanced red fluorescent protein (ERFP), expression of both vectors was detected simultaneously in live cells using fluorescent microscopy after incubation with fluorescein di-galactoside (FDG). In co-expressing cell populations, minK-lacZ cells (green) were imaged using the FITC filter while cGATA6-positive cells (ERFP, red color) were detected using a rhodamine filter. Staining for β-galactosidase activity revealed discrete clusters of minK-positive cells within the EBs.

Although minK is expressed in discrete cell clusters, expression of cGATA6 is restricted to a sub-population of minK-positive cells, recapitulating their expression patterns in vivo, as has been described. (S Kupershmidt et al. *Circ Res* 84 (1999) 146 and Wobus A M et al. *Ann NY Acad Sci* 752 (1995) 460). In fact, cells expressing minK extend from cGATA6-positive clusters and merge with nearby spontaneously contracting regions (FIG. 4). cGATA6-positive cell clusters are almost always separated from nearby spontaneously contracting regions. Although there is some heterogeneity with regard to the size and relative location of these cell clusters, the organization with respect to contracting regions is consistent. The EBs used in these experiments were generated as "hanging drops" so that the developmental conditions for each EB was as standardized as possible. The cellular arrangement depicted by these two molecular markers is strikingly similar to that of the cardiac conduction system in vivo, where a pacemaking node of cells is bridged with working (contracting) myocardium by specialized, rapidly conducting myocytes. The cGATA6 enhancer is first expressed in these EBs at approximately day 5 of differentiation while minK expression is not detected until day 8 (when spontaneous contractions are first observed).

cGATA6 identifies pacemaking or "nodal" structures: In order to determine whether cGATA6 actually identifies pacemaking or "nodal" structures, EBs were incubated with a calcium-sensitive fluorescent dye (Calcium Green®) and imaged before and after the onset of spontaneous contractions. Fluorescent calcium-sensitive dyes are useful for demonstrating functional coupling as well as excitation propagation in vitro (Viatchenko-Karpiinski S et al. *Proc Natl Acad Sci USA* 96 (1999) 8259). Calcium-dependent depolarizations generated by nodal (pacemaking) myocytes are propagated throughout the heart to control myocardial contractions (Sauer H et al. *Am J Physiol Heart Circ Physiol* 281 (2001) H411).

For imaging calcium fluorescence, EBs were loaded with 10 μM of the membrane-permeant acetoxymethyl ester derivative of the fluorescent calcium indicator, CALCIUM GREEN® (Molecular Probes) for 30 min. at 37° C. The EBs were then washed and incubated for 1 hour in differentiation medium before images were acquired. Cells were imaged on a Diaphot TMD (Nikon) inverted microscope using the 20× objective. Images were captured using a digital camera (Roper Scientific) and analyzed with Metamorph Software.

It was determined that cGATA6 identifies pacemaking or "nodal" structures by loading EBs with a calcium-sensitive fluorescent dye (CALCIUM GREEN®) and imaging them while they are spontaneously contracting. cGATA6-positive clusters were found to display a higher basal calcium concentration than surrounding cells. At day 6 of differentiation, prior to the onset of visible spontaneous contractions, rhythmic, spontaneous calcium oscillations are observed in GATA6-positive cell clusters. After the onset of spontaneous contractions (day 10 of differentiation), calcium oscillations are observed emitting from cGATA6-positive clusters, extending into contractile regions.

A representative region of an EB (6d of differentiation) isolated prior to the onset of visible spontaneous contractions demonstrated a cGATA6-positive cell cluster by red staining. Calcium imaging frames from the same EB region at rest and during depolarization were overlain on phase-contrast images of the same region. The same EB 5 days later demonstrated the cGATA6-positive cells. Calcium imaging frames from the same EB region at rest and during contraction were overlain on phase-contrast images of the same region. Calcium oscillations (green) could be clearly seen originating from the cGATA6-positive cell cluster (red). Calcium sparks are emitted from cGATA6-positive cell clusters prior to the onset of spontaneous contractions. These data demonstrate that cGATA6-positive cell clusters exhibit spontaneous, rhythmic calcium oscillations prior to the onset of visible contractions in EBs. The rhythmic calcium oscillations emitted from cGATA6-positive cell clusters into nearby contracting regions persists at least to days 10 and 20 of differentiation (last time point measured).

cGATA6-positive cell clusters are physically coupled to spontaneously contracting regions and control the rate of contraction in EBs: To determine whether cGATA6-positive clusters are functionally coupled with contracting regions, experiments were performed in which the cGATA6-positive cells were physically separated from nearby contracting regions. After identifying cGATA6-positive cell clusters near spontaneously contracting regions (FIG. 5A), spontaneous contractions were counted by direct visualization under the microscope. In order to separate cGATA6-positive cells from spontaneously contracting regions, a scalpel fixed to a micromanipulator (Eppendorf) was lowered into the EBs between cGATA6-positive and contracting regions and quickly pulled through so that there was complete separation of the two areas without any discernable tissue destruction (FIG. 5B). Spontaneous contractions were counted again after the separation.

As controls, cuts were made on the opposite side of spontaneously contracting regions, away from the cGATA6 clusters. Physically separating these two regions either reduces the spontaneous contraction rate from 56.5±10 to 17±7.5 contractions/min. (n=11) or causes cessation of spontaneous contractions (FIG. 5C). None of the control cuts caused a change in contraction rate. Thus it was shown that cGATA6-positive clusters are functionally coupled with contracting regions and that physical coupling between the two cell populations affects contraction rate.

Electrophysiological characteristics of the pacemaking/conducting cells: The electrophysiological characteristics of the pacemaking/conducting cells were examined on spontaneously contracting EBs (differentiation day 15) dissociated into single cells (FIG. 3A-F) and used for patch-clamp experiments. It is accepted that cardiac pacemaking cells exhibit a characteristic action potential waveform and express a prominent hyperpolarization-activated cation current ($I_f$, pacemaking current) (Cho H S et al., *J Physiol* 550 (2003) 169; Boyett M R et al., *Cardiovasc Res* 47 (2000) 658; Stieber J et al., *Proc Natl Acad Sci USA* 100 (2003) 15235).

On the day prior to recording, EBs were dispersed and plated onto glass coverslips coated with 0.1% gelatin. On the following day, coverslips were transferred to a recording chamber mounted on an inverted microscope (Nikon Diaphot-TMD) and superfused with extracellular recording solution. All experiments were conducted at room temperature (22-25° C.). Whole-cell voltage-clamp and current-clamp experiments were carried out using a standard Giga-seal patch-clamp method (Hamill O P et al. *Pflugers Arch* 391 (1981) 85). Recording electrodes were fabricated from 1.5 mm thin-walled borosilicate glass tubes (#7052. Garner Glass, Claremont, Calif.), using a Flaming-Brown microelectrode puller (P-97, Sutter Instruments, Novato, Calif.) and heat-polished before use. Each of the pipettes used had a tip resistance of 2-5 MΩ when filled with internal solution. Recordings were performed using an Axoclamp 2B patch-clamp amplifier (Axon Instruments, Union City, Calif.). Data were filtered at 2 kHz, and data were acquired using Clampex 8 software (Axon Instruments).

Cells were identified as minK- or cGATA6-positive using either the FITC or the rhodamine filters, respectively during fluorescence microscopy. Spontaneous action potentials were recorded from spontaneously contracting cells or were elicited by stimulation with a 2.5 ms, 200 pA square-wave current. Recordings were made 1 min. following establishment of the whole-cell configuration. For current-clamp recordings, the extracellular bath solution contained: 140 mM NaCl, 5.4 mM KCl, 1.8 mM $CaCl_2$, 1 mM $MgCl_2$, 10 mM glucose and 5 mM HEPES at pH 7.4 (with NaOH). The intracellular pipette solution contained: 140 mM KCl, 10 mM NaCl, 2 mM $MgCl_2$, and 5 mM HEPES at pH 7.3 (with KOH).

Voltage-gated calcium currents ($I_{Ca}$) were elicited in the whole-cell configuration by holding cells at −80 mV for 500 ms and then applying 10 mV steps (500 ms) from −80 to +60 mV and returning to the holding potential of −80 mV. When recording $I_{Ca}$ the extracellular solution contained 140 mM tetraethylammonium-chloride (TEA-Cl), 10 mM $CaCl_2$, 1 mM $MgCl_2$, 10 mM glucose, 5 mM 4-aminopyridine, and 10 mM HEPES at pH 7.4 (with TEA-OH). The intracellular pipette solution contained 140 mM CsCl, 2 mM $MgCl_2$, 10 mM EGTA, 5 mM Mg-ATP, and 10 mM HEPES at pH 7.3 (with CsOH).

Hyperpolarization-activated ($I_f$) currents were elicited by holding cells at −40 mV for 50 ms followed by 10 mV steps (2 sec) to −140 mV and returned to −40 mV (50 ms) after each step. Following the recording of $I_f$, cells were superfused with extracellular solution containing 10 mM cesium chloride. When measuring $I_f$, the extracellular solution was the same as that used for measuring action potentials (current-clamp) except for the addition of 2 mM $BaCl_2$, and 0.5 mM 4-aminopyridine. The intracellular pipette solution contained 10 mM NaCl, 130 mM K-aspartate, 2 mM $Na_2ATP$, 0.1 mM $Na_2GTP$, 2 mM $MgCl_2$, 1 mM EGTA, 10 mM HEPES, 10 mM tetraethylammonium chloride, at pH 7.3 (with KOH).

Isolated cells expressing both cGATA6 and minK were shown to display morphological and electrophysiologic characteristics of cardiac pacemaking/conducting cells. Referring to FIGS. 3(A)-(F), in FIG. 3(A) a representative cGATA6-minK co-positive cell displaying a "nodal" morphology (as described by Wu J et al., *Am J Physiol Heart Circ Physiol* 280 (2001) H1232) is shown. Of the isolated cells expressing both cGATA6 and minK, cells displaying a "nodal" morphology (FIG. 3A) exhibit action potential waveforms characteristic of cardiac nodal cells with a prominent diastolic (phase 4) depolarization (FIG. 3C).

In FIG. 3 (B) cGATA6-minK cells with morphologies similar to contracting atrial myocytes display atrial-like action potential waveforms (FIG. 3D). FIG. 3(E) presents representative traces from a cGATA6-minK co-positive cell demonstrating the inward hyperpolarization-activated cation current characteristic of nodal cells. (F) Current-voltage relationship for hyperpolarization-activated currents measured in cGATA6-minK co-positive cells before (triangles) and after (squares) treatment with 10 mM cesium chloride. Points represent mean values at each membrane potential error bars±standard error of the mean (SEM), n=16 cells. Remarkably, all GATA6-minK co-positive cells exhibit a significant cesium-sensitive hyperpolarization-activated cation current (FIGS. 3(E) and (F)), which is characteristic of cardiac pacemaking myocytes (as defined by Boyett M R, et al. *Cardiovasc Res* 47 (2000) 658).

Thus it was demonstrated that co-expression of the two molecular markers cGATA6 and minK in differentiating ES cells revealed a functional in vitro cardiac conduction system.

cGATA6-positive cell clusters act as pacemaking units that functionally couple with nearby contracting regions of EBs. Moreover, individual cells expressing these markers display electrophysiologic characteristics of cardiac pacemaking/conducting cells. The EB model system and the pacemaking/conducting cells identified by these markers can be used for studying the fundamental biology of cardiac pacemaking cells, designing targeted pharmaceutical agents, and developing novel cellular and tissue-engineered therapies.

Example 2

Isolation of GATA6 Populations

In another embodiment of the invention, pure populations of cGATA6-positive cells were generated by creating an ES cell population containing a vector in which expression of the neomycin resistance gene (neo) as a selectable marker was controlled by cGATA6 regulatory elements. In order to create the selection vector, pcDNA3.1(+)-neo was digested with Bcl1 and re-ligated. This resulted in the re-positioning of the neomycin resistance gene (neo) immediately downstream of the multiple cloning site (MCS). The proximal 1.5 kb (−1.5/0.0) region of the chicken GATA6 promoter/enhancer (cGATA6) was inserted between the Sal1 and BamHI sites in the MCS of the modified pcDNA3.1(+)-neo vector (with the Bcl1 fragment removed). In this newly formed vector, neo expression is controlled by the cGATA6 promoter. In order to enrich the population of cells containing the cGATA6-neo vector, linearized cGATA6-neo was co-transfected with linear pcDNA3.1(+)-hygro using LF2000 (Invitrogen). Transfected, undifferentiated ES cells were cultured for 7 days in ES growth medium containing 200 µg/ml, hygromycin (AG Scientific) prior to being used for experiments.

J1 ES cells containing the cGATA6-neo vector were differentiated using a suspension protocol as previously described. Briefly, 3×10⁶ ES cells were placed into a non-treated (tissue culture) Petri dish (Fisher), which contained differentiation medium and cultured for 3 days. After 3 days in suspension culture, EBs were plated onto tissue culture dishes (10 cm²) coated with 0.1% gelatin where they continued to develop. On day 7 of differentiation, EBs made from ES cells containing the cGATA6-neo vector were dispersed into single cells by incubating the EBs in trypsin for 5 min. followed by mechanical dissociation using a pipette. After 5 min. of centrifugation (1000 rpm), cells were suspended and plated onto 0.1% gelatin-coated dishes containing differentiation medium with 200 µg/mL G418 (Invitrogen). Each subsequent day, cells were washed multiple times with calcium/magnesium-free phosphate-buffered saline (PBS) and fresh medium containing 200 µg/mL G418 was added for a total of 7 days. After 7 days of selection, cells were cultured for 4-6 days in medium containing no G418. After this time, cells were passaged (using trypsin) and plated onto 0.1% gelatin-coated 35 mm dishes. Relative to the number of cells prior to selection, very few cells survived drug selection (FIG. 8A). Approximately 10-14 days after the completion of selection, colonies of cells with a similar morphology could be observed (FIG. 8B).

Cardiac pacemaking cells have characteristic electrophysiological properties including voltage-gated calcium currents carried primarily by T-type calcium channels as well as hyperpolarization-activated depolarizing (pacemaking) currents ($I_f$). The cGATA6-neo cells express voltage-gated calcium currents (FIG. 8C). The current-voltage relationship (FIG. 8D) indicates that T-type channels predominate (peak current at −20 mV). Selected cGATA6-neo cells also express the hyperpolarization-activated pacemaking current ($I_f$) (FIG. 8E-F). The cells and related results depicted in FIG. 8 were from cells passaged 1 time prior to electrophysiology such that they could be plated on slides. At the same time as passage onto slides, aliquots of the cells were harvested for the P0 RNA expression profile analysis described below.

Gene expression analysis: Gene expression analysis was performed in order to better understand the molecular phenotype of the pacemaking cells. Using real-time RT-PCR, the expression of 34 genes was examined using the primers set out on Table 1 following.

TABLE 1

RT-PCR Primers

| GENE | SENSE PRIMER | SEQ ID | ANTI-SENSE PRIMER | SEQ ID |
|---|---|---|---|---|
| Reference | | | | |
| 1. GAPDH | TCAAGAAGGTGGTGAAGCAG | 3 | CCCTGTTGCTGCTGTAGCCG | 4 |
| 2. Neo | TGAATGAACTGCAGGACGAG | 5 | ATACTTTCTCGGCAGGAGCA | 6 |
| 3. Oct 4 | | 7 | | 8 |
| Transcription Factors | | | | |
| 4. GATA4 | CCGGGCTGTCATCTCACTAT | 9 | GCCTGCGATGTCTGAGTGAC | 10 |
| 5. GATA6 | GCCAACTGTCACACCACAAC | 11 | TGTTACCGGAGCAAGCTTTT | 12 |
| 6. MEF2C | CTCCACCTCGGCTCTGTAAC | 13 | CTTGATGCTGAGGCTTTGAG | 14 |
| 7. Msx2 | AGGAAACACAAGACCAACCG | 15 | GCAGCCATTTTCAGCTTTTC | 16 |
| 8. MyoD | CACGACTGCTTTCTTCACCA | 17 | ATATCCCAGTTCCTGGGTC | 18 |
| 9. Nkx2.5 | TTAGGAGAAGGGCGATGACT | 19 | AGGTCCGAGACACCAGGCTA | 20 |
| 10. Tbx2 | GGGTCATCTGCTAGCCTCAG | 21 | TATGCTGGGAGAGGTGGAAC | 22 |
| 11. Tbx3 | AGGAGCGTGTCTGTCAGGTT | 23 | GCCATTACCTCCCCAATTTT | 24 |

TABLE 1-continued

RT-PCR Primers

| GENE | SENSE PRIMER | SEQ ID | ANTI-SENSE PRIMER | SEQ ID |
|---|---|---|---|---|
| 12. Tbx5 | ATGGTCCGTAACTGGCAAAG | 25 | TTCGTCTGCTTTCACGATG | 26 |
| Structural Proteins | | | | |
| 13. α-cardiac actin | TCTGAGATGTCTCTCTTA | 27 | CGTACAATGACTGATGAGAGA | 28 |
| 14. α-skeletal actin | GACAATCGACAATCGTGCTG | 29 | TCCACAGGGCTTTGTTTGAGT | 30 |
| 15. α-myosin heavy chain | GAAGATGCACGACGAGGAAT | 31 | CGAACGTTTATGTTTATTGTA | 32 |
| 16. β-myosin heavy chain | GGGCCTGAATGAGGAGTAGA | 33 | GTTGCAAAGGCTCCAGGTCTC | 34 |
| 17. myosin light chain-2a | CTCGGGAGGGTAAGTGTTCC | 35 | CATGCGGAAGGCACTCAGGCG | 36 |
| 18. myosin light chain-2v | GAGACCATTCTCAACGCATTC | 37 | GGAAAGGCTGCGAACATCTTC | 38 |
| 19. desmin | GTGAAGATGGCCTTGGATGT | 39 | TGGACTTCAGAACCCCTTTGG | 40 |
| 20. atrial natriuretic factor | TCTTTGCTTCTGCCCTCAGT | 41 | GTGATGGAGGCAGACGATTTG | 42 |
| Ion Channels and Connexins | | | | |
| 21. connexin 40 | CCTGAAACGTCCCTGTGTTT | 43 | TGAACAGGACAGTGAGCCAG | 44 |
| 22. connexin 43 | GAACACGGCAAGGTGAAGAT | 45 | GAGCGAGAGACACCAAGGAC | 46 |
| 23. connexin 45 | AGGCTGTCCTTGGTCAGAGA | 47 | TGTAACTCCAGTTCCAGGGG | 48 |
| 24. Cav1.2 (L-type $Ca^{2+}$) | ACGCCCAGCTCATGCCAACA | 49 | TAAGGCCACACAATTGGCAA | 50 |
| 25. Cav1.3 (T-type $Ca^{2+}$) | GGCTGAAGCTGGTGGTAGAG | 51 | CCCAGGTTGTCAAAGTTGTC | 52 |
| 26. Ryr2 (ryanodine receptor) | GCGAGCTGGCTACTATGACC | 53 | CGTTGCTAATGCTCACGAAA | 54 |
| 27. Ncx1 ($Na^+$-$Ca^{2+}$ exchanger) | AGATCAAGCATCTGCGTGTG | 55 | TGGAAGCTGGTCTGTCTCCT | 56 |
| 28. Scn5a ($Na^+$) | GTGATAACCTCCCAGTGCGT | 57 | AGGATACAACAGGGCACGTC | 58 |
| 29. Kir2.1 (inward rectifier $K^+$) | GAGGGAAGCATAGGTCGTTA | 59 | TGGAAGGTGCCAGGTTATGG | 60 |
| 30. KAch (Ach-gated $K^+$) | ACCCTGGTGGATCTCAAGTG | 61 | GGCCACACAGGGAGTGTAGT | 62 |
| 31. minK | GATCCAAGAAGCTGGAGCAC | 63 | CTCAGTGGTGCCCCTACAAT | 64 |
| 32. HCN1 | CAGCATGTCTGACCTCTGGA | 65 | TATCTTCTGGCGCATGTCAG | 66 |
| 33. HCN2 | CTGCGTGAGGAGATTGTGAA | 67 | GATCTCCCCGAAATAGGAGC | 68 |
| 34. HCN3 | CGTAGCTGGGTACCGTCAAT | 69 | ACTTGGTGTGGACAAGGAGG | 70 |
| 35. HCN4 | CTTCTGCTGTGTCACTGGGA | 71 | ATACTGCTTCCCCCAGGAGT | 72 |

Total RNA was isolated using the Qiagen RNeasy Kit and was reverse-transcribed into cDNA using Superscript III (Invitrogen). Real-time PCR was performed with the ABI Prism 7000 System Detection Sequence (SDS) and software (Applied Biosystems) using SYBR Green (Applied Biosystems) as the detector. Gene expression data are shown as the cycle threshold (the lower the number, the higher the gene expression). Gene expression comparisons were made using the delta, delta cycle threshold (CT) method—the CT was normalized to gapdh and then used for comparisons. The RT-PCR results for expression of 34 genes is presented in Table 2. The P0 cells are trypsinized cells before first passage. These cells were in culture (differentiation) for 24 days (7 as intact EBs+7 as dispersed EBs in selection+10 days following selection). 7d EBs were trypsinized and plated onto new dishes as single cells. They remained on these same dishes (17 days) until they were harvested for RNA or passaged 1 time onto coverslips for electrophysiology.

Also on Table 2 is data representing RNA expression from 42 day-old GATA6 cells that were passaged 5 times (GATA6-P5) when the second PCR analysis was performed. These cells were passaged at a split ratio of 1:2 every 3-4 days. The RNA expression profile is quite similar to that of P0 cells.

TABLE 2

Gene Expression in cGATA6-neo cells

| REFERENCE | RELATIVE EXPRESSION FOR P0 CELLS | CYCLE THRESHOLD- P0 | GATA6 P5 |
|---|---|---|---|
| 1. GAPDH |  | 14.9 | 14.5 |
| 2. Neo | **** | 22.2 | 19.7 |
| 3. Oct4 |  |  | 15.9 |
| *Transcription Factors* | | | |
| 4. GATA4 | **** | 21.8 | 22.2 |
| 5. GATA6 | **** | 20.7 | 20.2 |
| 6. MEF2C | ** | 27.7 | 27.6 |
| 7. Msx2 | ***** | 18.3 | 18.7 |
| 8. MyoD | * | 29.2 | 30.5 |
| 9. Nkx2.5 | *** | 24.3 | 25.7 |
| 10. Tbx2 | * | 29.2 | 31.1 |
| 11. Tbx3 | *** | 24.1 | 21.3 |
| 12. Tbx5 | ** | 27.3 | 29.0 |
| *Structural Proteins* | | | |
| 13. α-cardiac actin | **** | 21.0 | 21.7 |
| 14. α-skeletal actin | ***** | 17.5 | 17.1 |
| 15. α MHC | **** | 21.7 | 23.0 |
| 16. β MHC | **** | 24.0 | 23.6 |
| 17. MLC-2a | **** | 21.2 | 21.7 |
| 18. MLC-2v | — | >40 |  |
| 19. Desmin | **** | 21.1 | 20.1 |
| 20. ANF | * | 30.5 | 31.4 |
| *Ion Channels and Connexins* | | | |
| 21. Connexin 40 | * | 28.9 | 29.2 |
| 22. Connexin 43 | ***** | 18.7 | 18.8 |
| 23. Connexin 45 | *** | 25.4 | 25.9 |
| 24. Cav1.2 (L-type $Ca^{2+}$) | ** | 27.4 | 28.6 |
| 25. Cav1.3 (T-type $Ca^{2+}$) | *** | 24.4 | 25.3 |
| 26. Ryr2 (ryanodine receptor) | * | 28.9 | 26.1 |
| 27. Ncx1 ($Na^+$—$Ca^{2+}$ exchanger) | ** | 28.0 | 27.4 |
| 28. Scn5a ($Na^+$) | *** | 26.0 | 27.8 |
| 29. Kir2.1 (inward rectifier $K^+$) | * | 28.7 | 30.1 |
| 30. KAch (Ach-gated $K^+$) | **** | 23.3 | 24.7 |
| 31. minK | ** | 27.7 | 27.6 |
| 32. HCN-1 | * | 28.6 | 30.1 |
| 33. HCN-2 | *** | 24.1 | 22.8 |
| 34. HCN-3 | *** | 24.5 | 23.5 |
| 35. HCN-4 | * | 28.5 | 27.4 |

Average (n = 2 isolations) cycle thresholds are shown (lower numbers indicate a higher level of gene expression). Genes were grouped according to cycle thresholds into the following: 5 stars = <20, 4 stars = 20-24, 3 stars = 24-26, 2 stars = 26-28, and 1 star = >28.

In addition to expressing characteristic cardiac-specific markers, cGATA6-positive cells also express other genes that indicate these cells represent a primitive cardiac myocyte population. While the selected cells express an anticipated high level of gata6, they also express significant levels of the cardiac transcription factors nkx2.5 and gata4 (much more than mef2c). Because cells of the cardiac conduction system have been thought to display a partial skeletal transcriptional profile (Takebayashi-Suzuki K et al. *Dev Biol* 234 (2001) 390-401), myoD was examined and was found to be expressed in the cGATA6-neo cells. However, the most highly expressed transcription factor of the ones that were examined was msx2 (64-fold higher than nkx2.5), which is known to be expressed in cells of the specialized cardiac conduction system (Chan-Thomas P S et al. *Dev Dyn* 197 (1993) 203-16). While msx2 is involved in many processes such as limb development, it also has a significant role in tissue regeneration. The T-box transcription factors tbx2 and tbx3 are considered markers of primitive cardiac myocytes (Moorman A F & Christoffels V M *Novartis Found Symp* 250 (2003) 25-34; discussion 34-43, 276-9) with tbx3 marking regions of the proximal conduction system in the adult heart (Hoogaars W M et al. *Cardiovasc Res* 62 (2004) 489-99). In the cGATA6-neo cells, tbx3 is expressed at a high level (34-fold higher than tbx2 and 9-fold higher than tbx5).

cGATA6-neo cells express several cardiac structural and sarcomeric proteins. Of all the genes examined (except for gapdh), the most highly expressed was α-skeletal actin, which is expressed 12-fold higher than α-cardiac actin. Although β-myosin heavy chain (β-mhc) is expressed at a significant level, these cells express 5-fold more α- than β-mhc. With regard to the myosin light chain (mlc) isoforms, the atrial mlc-2a isoform is expressed a high level while expression of the ventricular mlc-2v isoform cannot be detected (up to 40 PCR cycles). Additionally, the cGATA6-neo cells express desmin, which is a marker of striated myocytes, and a very low level of atrial natriuretic factor (ant), which is considered to be an early marker of chamber (atrial or ventricular) working myocardium (Houweling A C et al. *Anat Rec* 266 (2002) 93-102).

The expression of 15 genes encoding ion channel subunits or connexins was examined. All three of the connexin isoforms found in cardiac myocytes, connexin 43, 45 and 40 were expressed in cGATA6-neo selected cells. Expression of the T-type calcium channel subunit gene cav 1.3 is 8-fold higher than the L-type calcium channel subunit cav1.2. cGATA6-neo cells express significant levels of genes encoding the cardiac ryanodine receptor (ryr2), the sodium-calcium exchanger (ncx1), the cardiac voltage-gated sodium channel (scn5a), and minK. Expression of kir3.1, which encodes the acetylcholine-gated potassium channel (KAch), is 42-fold higher than the expression of kir2.1, which encodes the inward rectifier potassium channel. With regard to the gene isoforms encoding the hyperpolarization-activated, cyclic nucleotide-gated (hcn) channels, which are involved in cardiac pacemaking, the hcn2 isoform is the most highly expressed. The relative expression of the 4 isoforms is hcn 2≧hcn 3>hcn 4≧hcn 1 (low level of expression).

Where surrogate marker selection is employed, the selection ultimately reflects the active transcriptional milieu of the cell but does not disturb this milieu. Thus, activation of the naturally occurring regulatory sequences is not disturbed nor is the resulting expression of the genes normally expressed. As such, the structural and regulatory genes normally generated continue to be generated and to participate in further regulatory cascades.

In cells transfected with linearized plasmid, genomic integration of the expression construct may occur leading to essentially stable transformation. However, where cells are selected on the basis of surrogate marker gene expression and are expanded to form a stable population committed to a particular lineage, it is not always necessary that the surrogate marker be integrated or even continue to be expressed. Thus, where the surrogate marker is expressed from an expression construct introduced into the cells on a vector that does not integrate or replicate in mammalian cells, the expression cassette may ultimately be lost to further cell division or may become transcriptionally silent. For transplantation purposes, the loss or transcriptional silence of the expression vector may, under some circumstances, be considered desirable.

Example 3

Modulated Differentiation of GATA6 Selected Cells

Adult nodal cardiac myocytes are able to maintain a primary myocardial (primitive heart tube) phenotype throughout development while surrounding myocytes differentiate into more differentiated, chamber myocardium (Christoffels V M et al. *Dev Biol* 223 (2000) 266-278; Hoogaars et al. 2004 supra; Moorman and Christoffels, 2003 supra). Paracrine factors and physical stimuli present in the heart during development contribute to the differentiation of the atrial and ventricular chamber myocardium (Brutsaert D L. *Physiol Rev* 83 (2003) 59-115; Brutsaert D L et al. *Cardiovasc Res* 38 (1998) 281-290; Chien K R et al. *Faseb J* 5 (1991) 3037-3046; MacKenna D, Summerour S R, Villarreal F J. *Cardiovasc Res.* 46 (2000) 257-63). In order to assess if cGATA6 cells are responsive to known cardiac differentiation and growth factors, cGATA6 cells were cultured in the presence of specialized media originally developed by William Claycomb for maintaining the differentiated phenotype of murine HL-1 cardiomyocytes ("Claycomb Medium", Commercially available as Cat. No. 51800, JRH Biosciences, Lenexa, Kans., US). This media formulation was described essentially in Claycomb et al. *Proc Natl Acad Sci USA* 95(6) (1998) 2979-84 and consists of the components of Table 3.

TABLE 3

Formulation of Claycomb Medium

| COMPONENT | AMOUNT |
| --- | --- |
| Total Protein | 261 µg/mL |
| Bovine albumin | 48.85 mg/L |
| Nonessential amino acids | 0.1 mM |
| Fetuin | 165 mg/L |
| Transferrin | 31.8 mg/L |
| Retinoic acid | 300 µg/L |
| Human Insulin (recombinant) | 15 µg/L |
| Long ™ R³IGF-1 (recombinant) | 0.1 µg/L |
| Long ™ EGF (recombinant) | 0.1 µg/L |
| Cholesterol | 1.96 mg/L |
| Linoleic acid | 0.78 mg/L |
| γ-oleyl-β-pal-α-phosphatidylcholine | 1.96 mg/L |
| Ascorbic acid | 0.3 mM |
| Norepinephrine | 100 µM |
| L-glutamine | 2 mM |
| Penicillin-Streptomycin (optional) | 100 units/mL-100 µg/mL |
| Fetal Bovine Serum (FBS) | 10% |

The basal medium for Claycomb Medium is DMEM. Complete formulation for Claycomb Medium provided by JRH Biosciences, Lenexa, KS.

Certain of the factors contained in Claycomb Medium such as retinoic acid, norepinephrine, and ascorbic acid have been variously shown to induce the differentiation of cardiac myocytes (Karliner J S and Simpson P C. *Basic Res Cardiol* 83 (1988) 655-663; Maki T et al. *J Clin Invest* 97 (1996) 656-663; Takahashi T et al. *Circulation* 107 (2003) 1912-1916; White S M, Constantin P E, and Claycomb W C. *Am J Physiol Heart Circ Physiol* 286 (2004) H823-829; Wobus A M, Rohwedel J, Maltsev V, and Hescheler J. *Ann NY Acad Sci* 752 (1995) 460-469; Xavier-Neto J et al. *Development* 126 (1999) 2677-2687).

Culturing cGATA6 cells in the presence of Claycomb Medium for 8 days (2 passages) resulted in distinct changes in morphology. The most notable change was the increase in the morphological homogeneity of the cGATA6 cell population, which normally contains very small (embryonic stem cell-like) and somewhat larger, more differentiated cells that grow in separate colonies. After the addition of Claycomb Medium, no small cells could be found.

Not only were there changes in the morphology of the cGATA6 cells after being cultured in Claycomb Medium, but there were also changes in their gene expression pattern that indicative of chamber myocardium differentiation as shown in Table 4. The most dramatic change observed was with regard to expression of oct4, which is a marker of stem cells (Buehr M et al. *Biol Reprod* 68 (2003) 222-229; Nichols J. et al. *Cell* 95 (1998) 379-391). There was a 99% reduction in oct4 (stem cell marker) expression in cGATA6 cells cultured in Claycomb Medium, indicating a loss of pluripotency. Moreover, there was a 73% reduction in msx2 expression, which indicates less regenerative capacity, if these cells are truly primitive myocytes. Expression of the cardiac transcription factors associated more with atrial and ventricular chamber myocardium (mef2c, gata4, and tbx5) were all induced. While the expression of gata6 was upregulated 10-fold following exposure to Claycomb Medium, the neomycin resistance gene (neo), which is a marker for the cGATA6 enhancer, was downregulated by 94%. This difference between gata6 and neo expression is indicative of the differences between the endogenous promoter/enhancer elements and the cGATA6 enhancer.

The only significant changes in sarcomeric or structural gene expression following exposure to Claycomb Medium were a 12-fold induction of sarcomeric α-cardiac actin and a 24-fold induction in the expression of the intermediate filament desmin. With regard to ion channels, treatment with Claycomb Medium caused an increase in the expression of both the T-(cav3.1) and L-type (cav1.2) voltage-gated calcium channel subunits with a concomitant decrease in expression of hcn-2 and -3, which are subunits for the hyperpolarization-activated ion current ($I_f$). Additionally, there was a 24-fold induction in the expression of the gap junction protein connexin 43, which is more highly expressed in the chamber myocardium, and is virtually absent from the SA and AV nodes (Jalife J, Morley G E, and Vaidya D. *J Cardiovasc Electrophysiol* 10 (1999) 1649-1663. Van Kempen M J, Vermeulen J L, Moorman A F, Gros D, Paul D L, and Lamers W H. *Cardiovasc Res* 32 (1996) 886-900). The most impressive change in gene expression patterns after the addition of Claycomb Medium was in the relationship of the subunits for the acetylcholine-gated potassium channel (kir3.1) and the inward rectifier potassium channel (kir2.1). Although atrial myocytes express acetylcholine-gated potassium channels, they are more highly expressed by nodal myocytes because the SA and AV nodes are the primary sites of parasympathetic innervation in the heart (Bettahi I, Marker C L, Roman M I, and Wickman K. *J Biol Chem* 277 (2002) 48282-48288; Demir S S, Clark J W, and Giles W R. *Am J Physiol* 276 (1999) H2221-2244). After being cultured in Claycomb Medium, there was dramatic reduction in kir3.1 expression with a concomitant 36-fold induction of kir2.1, which is expressed by contractile, non-nodal cardiac myocytes.

TABLE 4

Gene Expression in cGATA6-neo cells after long-term culture and with changes to culture conditions

| REFERENCE | RELATIVE EXPRESSION FOR P14 CELLS | +CLAYCOMB MEDIUM |
|---|---|---|
| 1. GAPDH | 14.4 | 14.5 |
| 2. Neo | 21.2 | 25.4 |
| 3. Oct4 | 15.4 | 23.1 |
| Transcription Factors | | |
| 4. GATA4 | 21.7 | 20.4 |
| 5. GATA6 | 21.1 | 17.8 |
| 6. MEF2C | 28.3 | 23.1 |
| 7. Msx2 | 20.4 | 22.4 |
| 8. MyoD | 28.0 | 24.3 |
| 9. Nkx2.5 | 26.6 | 26.6 |
| 10. Tbx2 | 34.8 | 34.1 |
| 11. Tbx3 | 22.7 | 21.8 |
| 12. Tbx5 | 30.4 | 26.2 |
| Structural Proteins | | |
| 13. α-cardiac actin | 23.3 | 19.8 |
| 14. α-skeletal actin | 20.2 | 20.6 |
| 15. αMHC | 22.3 | 25.3 |
| 16. βMHC | 24.7 | 25.0 |
| 17. MLC-2a | 22.0 | 22.3 |
| 18. MLC-2v | 24.2 | 26.7 |
| 19. Desmin | 21.1 | 16.6 |
| 20. ANF | 31.6 | 31.4 |
| Ion Channels and Connexins | | |
| 21. Connexin 40 | 31.1 | 28.7 |
| 22. Connexin 43 | 21.9 | 17.4 |
| 23. Connexin 45 | 24.5 | 23.2 |
| 24. Cav1.2 (L-type $Ca^{2+}$) | 29.1 | 26.0 |
| 25. Cav3.1 (T-type $Ca^{2+}$) | 25.1 | 22.6 |
| 26. KAch (Ach-gated $K^+$) | 22.2 | 30.4 |
| 27. Kir2.1 (inward rectifier) | 29.5 | 24.4 |
| 28. minK | 29.4 | 27.9 |
| 29. HCN-1 | 32.6 | 33.1 |
| 30. HCN-2 | 22.7 | 25.0 |
| 31. HCN-3 | 23.9 | 26.9 |
| 32. HCN-4 | 29.9 | 29.2 |

Data are listed as cycle thresholds obtained using real-time RT-PCR. Lower numbers indicated a higher level of gene expression (exponentially).

Example 4

Use of GATA6 Selected Cells as Pacing Cells for Contracting Myocytes

Aggregates of cGATA6 cells were shown to spontaneously depolarize. Cardiac pacemaking by the SA node is accomplished by a highly organized, heterogeneous population of specialized cells that are electrically coupled with the atrial myocardium (Boyett M R et al. *J Cardiovasc Electrophysiol* 14 (2003) 104-106; Boyett M R, Honjo H, and Kodama I. *Cardiovasc Res* 47 (2000) 658-687).

In order to test whether cGATA6 cells were capable of coupling with and pacing contracting cardiac myocytes, cGATA6 cells were co-cultured with HL-1 cardiac myocytes. HL-1 cells are immortalized atrial cardiac myocytes that spontaneously contract and maintain a differentiated phenotype through many passages in culture (Claycomb et al., 1998 supra).

In an attempt to simulate a nodal architecture and to generate a critical mass of cells capable of electrically pacing a monolayer of HL-1 cells, cGATA6 cell aggregates were made using the same technique used to make hanging-drop embryoid bodies. Approximately 500 cGATA6 cells selected and passaged (16×) were placed in 30 L drops in dishes, which were inverted for 2 days, allowing the formation of cellular aggregates. These cGATA6 cell aggregates were plated onto monolayers of HL-1 cells (approximately 75% confluent) and cultured for 1-3 days. The co-cultures were then incubated in the fluorescent, calcium-sensitive dye Calcium Greene® and imaged for spontaneous calcium transients. Of 10 cGATA6 aggregates imaged, 4 displayed spontaneous calcium transients and, within the limitations of the imaging system used, appeared to be coupled to the adjacent HL-1 cells. These experiments clearly demonstrate that aggregates of cGATA6 cells are capable of spontaneously depolarizing.

Example 5

Use of Isolated PCS Cells in Transplantation

Due to the obvious consequences of serious heart disease and the absence of sub-heroic therapies, cell transplantation for correction of various defects in the heart has been of great interest. Cell transplantation, termed "cellular cardiomyoplasty", for the repair of damage due to myocardial infarction been the subject of 10 Phase I clinical trials to date, involving over 100 patients. (Lee M S and Makkar R R, *Ann Intern Med* 140 (2004) 729-737). Because spontaneously contracting cardiomyocytes can be coaxed to develop from cells of various origins including bone marrow, skeletal myoblasts, and human embryonic stem cells, cellular cardioplasty for treatment of ischemia is relatively straightforward.

However, there is also considerable interest in the development of "biological pacemakers" for the correction of defects in the cardiac pacemaking and conducting system that result in arrhythmias such as sinus node dysfunction, atrial and ventricular tachyarrhythmias, and complete heart block or that which would otherwise require the implantation of pacemaker hardware. This is a more complex issue, in part because the highly specific differentiation characteristics of pacing cells limit the potential sources of such cells. In addition, in order to allow the transplanted cells to collaborate with existing pacing cells and exploit the existing conductivity pathway that controls synchronized contraction, such cells will need to be transplanted into precise locations.

Several approaches have been attempted for the generation of pacemaking cells by transfection with structural genes encoding the protein subunits of the ion or nucleotide-gated channels. In one study, differentiated ventricular myoblasts were converted to pacing cells by dominant negative suppression of the endogenous Kir2-encoded inward-rectifier potassium channels normally expressed by ventricular cells. When such cells were transplanted into the left ventricular cavity, the foci of induced pacemakers caused the heartbeat to originate from the ventricles. (Miake et al. *Nature* 419 (2002) 132). In a similar vein, Gepstein et al. *Am J Heart Circ Physiol* 286 (2004) H815-H822, described the use of libroblasts transfected to express the voltage-gated potassium channel Kv1.3 in order to form a population of cells able interact electrophysiologically with cardiomyocytes. These genetically altered cells however, impose a safety concern when considered for transplantation.

The spontaneous rhythmic activity in the mammalian heart depends on the hyperpolarization-activated "pacemaker" currents ($I_f$) produced by hyperpolarization-activated, cyclic nucleotide gated (HCN) channels. Gene transfer of structural genes encoding the α (hyperpolarization-activated cyclic nucleotide—gated [HCN2]) and/or β (minK-related peptide 1 [MiRP1]) subunits of the human endogenous pacemaker currents has been attempted in order to generate biological pacemakers. See e.g. Qu J et al. *Circulation* 107 (2003) 1106-1109.

One embodiment of the present invention provides a different approach. Instead of transfecting otherwise committed cells with genes that encode a single structural feature of pacemaking or conducting cells, the present invention permits the isolation and expansion of stem cells that will differentiate or have differentiated to either a pacemaking or conducting phenotype by surrogate marker selection. As aforementioned, the surrogate marker expressed as a consequence of activity on the promoter enhancer elements, such as for example the present GATA6 enhancer based selection merely exploits the desired transcriptional milieu to report which cells have committed to this phenotype. The underlying expression of the native genes is not necessarily altered. After the cells have committed to this phenotype and are thus selected and enriched, reporter expression is no longer required. The system does not necessitate the use of strong promoters that may become promiscuously associated with the expression of other genes through crossover events even where integration may occur as a consequence of multiple rounds of selection. Following selection and enrichment, populations of stem cells selected for expression from the enhancers may be expanded and transplanted into either the SA or AV node.

Example 6

Use of Isolated PCS Cells in Determining the Pharmacologic Effects of Compounds on Cells of the Mammalian Cardiac Conducting System A population of embryonic stem cells that have been selected for expression of the developmental stage specific proteins GATA6, minK, and combinations thereof can be used to model the pharmacological effects of new and existing compounds on the PCS. Thus model system can be used both to test for compounds able to affect the depolarization and conductivity rate within in the PCS as well as those may have an adverse toxic effect on the function of the system including the potential for adverse effects on the developing cardiovascular system in utero.

Three different types of membrane voltage channels are important in causing the voltage changes of the action potential in the heart: 1) fast sodium ($Na^+$) channels; 2) slow-calcium ($Ca^{++}$) channels, and 3) potassium ($K^+$) channels. Sinoatrial node cardiomyocytes differ considerably from working cardiomyocytes in the function of their membrane channels. Unlike most other cells that elicit action potentials (e.g., nerve cells, muscle cells), in SA cells the depolarizing current is carried primarily by relatively slow, inward $Ca^{++}$ currents instead of by fast $Na^+$ currents. Unlike most other cells having membrane voltage channels, there are no fast $Na^+$ currents operating in SA nodal cells. A number of cardioactive drugs ultimately affect the cardiac conduction system including through affects on the ion channels. In fact, most deaths from poisoning with cardioactive drugs such as rate limiting calcium channel blockers, non-selective beta-adrenoceptor antagonists and digitalis glycosides are from cardiac dysrhythmias.

The present system provides a model of the effect of cardioactive drugs on both conducting and contracting cardiomyocytes as well as the interactions between the two. The system also provides a model for testing of drug interactions.

In a further embodiment, a model is provided for the identification of novel receptors expressed on the cell surface of the various different populations of cells coexisting or isolated from the in vitro PCS system of the present invention. The identification of such receptors allows for the development of new drugs able to target these specific receptors.

In one embodiment of the invention, multiple mutations can be made to the undifferentiated ES cells utilizing markers such as those described herein. The effects of these mutations can be studied in the developing EBs with regard to cellular organization, coupling, electrical behavior, and other properties. This system would allow for high throughput screening of EBs containing mutations (single or multiple) and how drugs or novel peptides affect the formation and function of this in vitro cardiac conduction system.

The examples and embodiments described herein are for illustrative purposes only, and various modifications will be apparent to those of skill in the art, the invention to be limited only by the scope of the appended claims. All publications, patents and patent applications cited herein are hereby incorporated by reference as if set forth in their entirety herein.

We claim:

1. A pure, isolated population of cardiac pacemaking cells that after multiple cell passages retain one or more cardiac pacemaking characteristics selected from the group consisting of expression of a voltage-gated calcium current and expression of a hyperpolarization-activated pacemaking current (If), wherein the cells are derived from mouse pluripotent embryonic stem cells by surrogate marker selection based on activity of the GATA6 promoter and enhancer, as set forth in SEQ ID No: 1.

* * * * *